(12) United States Patent
Yuen et al.

(10) Patent No.: US 10,126,830 B2
(45) Date of Patent: Nov. 13, 2018

(54) USER IDENTIFICATION VIA MOTION AND HEARTBEAT WAVEFORM DATA

(71) Applicant: Fitbit, Inc., San Francisco, CA (US)

(72) Inventors: Shelten Gee Jao Yuen, Berkeley, CA (US); James Park, Berkeley, CA (US); Atiyeh Ghoreyshi, San Francisco, CA (US); Anjian Wu, Colma, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 15/812,879

(22) Filed: Nov. 14, 2017

(65) Prior Publication Data

US 2018/0067565 A1 Mar. 8, 2018

Related U.S. Application Data

(63) Continuation of application No. 15/603,305, filed on May 23, 2017, now Pat. No. 9,851,808, which is a
(Continued)

(51) Int. Cl.
*G06F 3/01* (2006.01)
*G06K 9/00* (2006.01)
(Continued)

(52) U.S. Cl.
CPC ............ *G06F 3/017* (2013.01); *A61B 5/0002* (2013.01); *A61B 5/02416* (2013.01);
(Continued)

(58) Field of Classification Search
CPC .......... G06F 3/017; G06F 19/00; G06F 1/163; G06F 21/32; G06K 9/00885; G06K 9/00342; G06K 9/0053; G06K 2009/00939; G06K 9/00335; G01S 19/19; G01S 19/00; G06Q 50/01; A61B 5/11; A61B 5/6802; A61B 5/1118; A61B 5/7475; A61B 5/742; A61B 5/0402; A61B 5/0002; A61B 5/7257; A61B 5/725; A61B 5/02416;
(Continued)

(56) References Cited

U.S. PATENT DOCUMENTS 6,583,369 B2 6/2003 Montagnino et al.
8,008,996 B2 8/2011 Chen et al.
(Continued)

FOREIGN PATENT DOCUMENTS

EP 1 721 237 8/2012

OTHER PUBLICATIONS

Terry, Ian Michael et al. "GeoFit: Verifiable Fitness Challenges", 2014 IEEE 11th International Conference on Mobile Ad Hoc and Sensor Systems. (Year: 2014).*
(Continued)

*Primary Examiner* — Darren B Schwartz
(74) *Attorney, Agent, or Firm* — Weaver Austin Villeneuve & Sampson LLP

(57) ABSTRACT

The disclosure relates to methods, devices, and systems to identify a user of a wearable fitness monitor using data obtained using the wearable fitness monitor. Data obtained from motion sensors of the wearable fitness monitor and data obtained from heartbeat waveform sensors of the wearable fitness monitor may be used to identify the user.

20 Claims, 19 Drawing Sheets

Related U.S. Application Data continuation of application No. 15/231,627, filed on Aug. 8, 2016, now Pat. No. 9,693,711.

(60) Provisional application No. 62/202,773, filed on Aug. 7, 2015.

(51) Int. Cl.

| | | |
|---|---|---|
| G06F 19/00 | (2018.01) | |
| G06F 1/16 | (2006.01) | |
| G01S 19/19 | (2010.01) | |
| G06Q 50/00 | (2012.01) | |
| G01S 19/00 | (2010.01) | |
| A61B 5/11 | (2006.01) | |
| A61B 5/00 | (2006.01) | |
| G01C 22/00 | (2006.01) | |
| A61B 5/0402 | (2006.01) | |
| G09B 5/02 | (2006.01) | |
| A63B 24/00 | (2006.01) | |
| A61B 5/024 | (2006.01) | |
| G06F 21/32 | (2013.01) | |
| G01P 13/00 | (2006.01) | |
| G01P 1/02 | (2006.01) | |
| A61B 5/117 | (2016.01) | |
| A63B 69/36 | (2006.01) | |
| A61B 5/103 | (2006.01) | |
| A61B 5/0404 | (2006.01) | |
| A61B 5/1172 | (2016.01) | |

(52) U.S. Cl.
CPC ........ *A61B 5/02438* (2013.01); *A61B 5/0402* (2013.01); *A61B 5/11* (2013.01); *A61B 5/112* (2013.01); *A61B 5/117* (2013.01); *A61B 5/1112* (2013.01); *A61B 5/1118* (2013.01); *A61B 5/1123* (2013.01); *A61B 5/441* (2013.01); *A61B 5/681* (2013.01); *A61B 5/6802* (2013.01); *A61B 5/725* (2013.01); *A61B 5/7257* (2013.01); *A61B 5/7264* (2013.01); *A61B 5/7267* (2013.01); *A61B 5/7271* (2013.01); *A61B 5/742* (2013.01); *A61B 5/7475* (2013.01); *A63B 24/0062* (2013.01); *G01C 22/006* (2013.01); *G01P 1/02* (2013.01); *G01P 13/00* (2013.01); *G01S 19/00* (2013.01); *G01S 19/19* (2013.01); *G06F 1/163* (2013.01); *G06F 19/00* (2013.01); *G06F 21/32* (2013.01); *G06K 9/00342* (2013.01); *G06K 9/00885* (2013.01); *G06Q 50/01* (2013.01); *G09B 5/02* (2013.01); *A61B 5/0022* (2013.01); *A61B 5/0024* (2013.01); *A61B 5/0404* (2013.01); *A61B 5/1032* (2013.01); *A61B 5/1172* (2013.01); *A61B 5/6844* (2013.01); *A61B 2560/0223* (2013.01); *A61B 2562/0219* (2013.01); *A63B 69/36* (2013.01); *G06K 9/0053* (2013.01); *G06K 9/00335* (2013.01); *G06K 2009/00939* (2013.01)

(58) Field of Classification Search
CPC . A61B 5/7267; A61B 5/02438; A61B 5/1112; A61B 5/112; A61B 5/441; A61B 5/7264; A61B 5/1123; A61B 5/681; A61B 5/117; A61B 5/1032; A61B 5/0404; A61B 5/0024; A61B 5/0022; A61B 5/6844; A61B 5/1172; A61B 2560/0223; A61B 2562/0219; G01C 22/006; G09B 5/02; A63B 24/0062; A63B 69/36; G01P 13/00; G01P 1/02
See application file for complete search history.

(56) References Cited

U.S. PATENT DOCUMENTS

| | | | |
|---|---|---|---|
| 8,447,704 B2 | 5/2013 | Tan et al. | |
| 8,922,342 B1 | 12/2014 | Ashenfelter et al. | |
| 8,983,637 B2* | 3/2015 | Glode | G06F 19/3481 700/91 |
| 9,159,213 B1 | 10/2015 | Chun et al. | |
| 9,667,353 B2 | 5/2017 | Åstrand et al. | |
| 9,693,711 B2 | 7/2017 | Yuen et al. | |
| 9,750,435 B2 | 9/2017 | Jun | |
| 9,782,075 B2 | 10/2017 | Redei | |
| 9,851,808 B2 | 12/2017 | Yuen et al. | |
| 2002/0138768 A1 | 9/2002 | Murakami et al. | |
| 2003/0061172 A1 | 3/2003 | Robinson | |
| 2003/0190062 A1* | 10/2003 | Noro | A61B 5/022 382/124 |
| 2004/0230105 A1 | 11/2004 | Geva et al. | |
| 2005/0281439 A1 | 12/2005 | Lange | |
| 2006/0025282 A1* | 2/2006 | Redmann | A61B 5/103 482/8 |
| 2006/0080525 A1 | 4/2006 | Ritter et al. | |
| 2006/0136744 A1 | 6/2006 | Lange | |
| 2007/0002141 A1 | 1/2007 | Lipton et al. | |
| 2007/0142715 A1 | 6/2007 | Banet et al. | |
| 2007/0142868 A1 | 6/2007 | Moon et al. | |
| 2007/0260511 A1* | 11/2007 | Bender, II | G06Q 30/02 705/14.13 |
| 2007/0263907 A1 | 11/2007 | McMakin et al. | |
| 2007/0293781 A1 | 12/2007 | Sims et al. | |
| 2008/0294019 A1 | 11/2008 | Tran | |
| 2009/0203972 A1 | 8/2009 | Heneghan et al. | |
| 2009/0241174 A1 | 9/2009 | Rajan et al. | |
| 2009/0319221 A1 | 12/2009 | Kahn et al. | |
| 2010/0113950 A1 | 5/2010 | Lin et al. | |
| 2010/0207721 A1 | 8/2010 | Nakajima et al. | |
| 2010/0331145 A1 | 12/2010 | Lakovic et al. | |
| 2010/0331903 A1 | 12/2010 | Zhang et al. | |
| 2011/0004072 A1 | 1/2011 | Fletcher et al. | |
| 2011/0032105 A1 | 2/2011 | Hoffman et al. | |
| 2011/0032139 A1 | 2/2011 | Benitez et al. | |
| 2011/0257554 A1 | 10/2011 | Banet et al. | |
| 2012/0007713 A1 | 1/2012 | Nasiri et al. | |
| 2012/0068820 A1 | 3/2012 | Mollicone et al. | |
| 2012/0083705 A1 | 4/2012 | Yuen et al. | |
| 2012/0179636 A1 | 7/2012 | Galiana et al. | |
| 2012/0274508 A1 | 11/2012 | Brown et al. | |
| 2012/0296455 A1 | 11/2012 | Ohnemus et al. | |
| 2012/0316455 A1 | 12/2012 | Rahman et al. | |
| 2013/0041856 A1 | 2/2013 | Benitez et al. | |
| 2013/0106684 A1 | 5/2013 | Weast et al. | |
| 2013/0158686 A1* | 6/2013 | Zhang | G01C 22/006 700/91 |
| 2013/0166048 A1 | 6/2013 | Werner et al. | |
| 2013/0204410 A1 | 8/2013 | Napolitano | |
| 2013/0227678 A1 | 8/2013 | Kang et al. | |
| 2013/0268236 A1* | 10/2013 | Yuen | A61B 5/0002 702/160 |
| 2013/0281805 A1 | 10/2013 | Mason et al. | |
| 2014/0059066 A1* | 2/2014 | Koloskov | G06F 17/30017 707/758 |
| 2014/0085050 A1 | 3/2014 | Luna | |
| 2014/0089672 A1 | 3/2014 | Luna et al. | |
| 2014/0099614 A1 | 4/2014 | Hu et al. | |
| 2014/0157209 A1 | 6/2014 | Dalal et al. | |
| 2014/0164611 A1 | 6/2014 | Molettiere et al. | |
| 2014/0266860 A1 | 9/2014 | Blumrosen et al. | |
| 2014/0275850 A1 | 9/2014 | Venkatraman et al. | |
| 2014/0275852 A1 | 9/2014 | Hong et al. | |
| 2014/0327515 A1 | 11/2014 | Luna et al. | |
| 2015/0035643 A1 | 2/2015 | Kursun | |
| 2015/0119728 A1 | 4/2015 | Blackadar et al. | |
| 2015/0161876 A1 | 6/2015 | Castillo | |
| 2015/0168365 A1 | 6/2015 | Connor | |
| 2015/0242605 A1 | 8/2015 | Du et al. | |
| 2015/0254575 A1 | 9/2015 | Nere et al. | |
| 2015/0272483 A1 | 10/2015 | Etemad et al. | |

(56) References Cited

U.S. PATENT DOCUMENTS

| | | |
|---|---|---|
| 2015/0301608 A1 | 10/2015 | Nagaraju et al. |
| 2015/0305674 A1 | 10/2015 | McPherson et al. |
| 2015/0342489 A1 | 12/2015 | Bhaumik et al. |
| 2016/0189451 A1 | 6/2016 | Yoo et al. |
| 2016/0378235 A1 | 12/2016 | Dow et al. |
| 2017/0032168 A1 | 2/2017 | Kim |
| 2017/0035327 A1 | 2/2017 | Yuen et al. |
| 2017/0035328 A1 | 2/2017 | Yuen et al. |
| 2017/0038848 A1 | 2/2017 | Yuen et al. |
| 2017/0039358 A1 | 2/2017 | Yuen et al. |
| 2017/0189755 A1* | 7/2017 | McKirdy ........... A63B 24/0075 |
| 2017/0231519 A1 | 8/2017 | Westover et al. |
| 2017/0235935 A1 | 8/2017 | Song et al. |
| 2017/0255273 A1 | 9/2017 | Yuen et al. |

OTHER PUBLICATIONS

Saeb Sohrab, et al. "Making Activity Recognition Robust against Deceptive Behavior", Dec. 11, 2015, PLoS One. (Year: 2015).*
U.S. Office Action, dated Nov. 18, 2016, issued in U.S. Appl. No. 15/231,620.
U.S. Final Office Action, dated Apr. 25, 2017, issued in U.S. Appl. No. 15/231,620.
U.S. Notice of Allowance, dated Feb. 23, 2017, issued in U.S. Appl. No. 15/231,636.
U.S. Notice of Allowance, dated Oct. 23, 2017, issued in U.S. Appl. No. 15/603,305.
U.S. Office Action, dated Dec. 19, 2016, issued in U.S. Appl. No. 15/231,636.
U.S. Final Office Action, dated May 3, 2017, issued in U.S. Appl. No. 15/231,636.
U.S. Office Action, dated Dec. 7, 2016, issued in U.S. Appl. No. 15/231,641.
U.S. Final Office Action, dated Apr. 20, 2017, issued in U.S. Appl. No. 15/231,641.
"Activator is One of the Best Cydia iPhone Hacks | Control your iPhone with Gestures," iphone-tips-and-advice.com, [retrieved on Jul. 9, 2013 at http://www.iphone-tips-and-advice.com/activator.html], 10 pp.
Chudnow, Alan (Dec. 3, 2012) "Basis Wristband Make Its Debut," *The Wired Self Living in a Wired World*, published in Health [retrieved on Jul. 22, 2013 at http://thewiredself.com/health/basis-wrist-band-make-its-debut/], 3pp.
DesMarais, Christina (posted on Sep. 3, 2013) "Which New Activity Tracker is Best for You?" *Health and Home, Health & Fitness, Guides & Reviews*, [Retrieved on Sep. 23, 2013 at http://www.techlicious.com/guide/which-new-activity-tracker-is-right-for-you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 10 Owner's Manual (Aug. 2012), Garmin Ltd., 10 pp.
Forerunner® 110 Owner's Manual, (2010) "GPS-Enabled Sport Watch," Garmin Ltd., 16 pp.
Forerunner® 201 personal trainer owner's manual, (Feb. 2006) Garmin Ltd., 48 pp.
Forerunner® 205/305 Owner's Manual, GPS-enabled trainer for runners, (2006-2008), Garmin Ltd., 80 pp.
Forerunner® 210 Owner's Manual, (2010) "GPS-Enabled Sport Watch," Garmin Ltd., 28 pp.
Forerunner® 301 personal trainer owner's manual, (Feb. 2006) Garmin Ltd., 66 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 405CX Owner's Manual, "GPS-Enabled Sports Watch With Wireless Sync," (Mar. 2009), Garmin Ltd., 56 pp.
Forerunner® 410 Owner's Manual, (Jul. 2012) "GPS-Enabled Sport Watch With Wireless Sync," Garmin Ltd., 52 pp.
Forerunner® 50 with ANT+Sport™ wireless technology, Owner's Manual, (Nov. 2007) Garmin Ltd., 44 pp.
Forerunner® 910XT Owner's Manual, (Jan. 2013) Garmin Ltd., 56 pp.
Garmin Swim™ Owner's Manual (Jun. 2012), 12 pp.
Lara et al. (2013) "A Survey on Human Activity Recognition using Wearable Sensors," *IEEE Communications Surveys & Tutorials, Third Quarter 2013*, 15(3):1192-1207.
Lark/Larkpro, User Manual, (2012) "What's in the box," *Lark Technologies*, 7 pp.
Larklife, User Manual, (2012) *Lark Technologies*, 7 pp.
Mills, C. (2015) "Paying for stuff with your heartbeat is now a thing," GIZMODO (Published online, Aug. 12, 2015), 2pp.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N.D. User Manual, Polar® Listen to Your Body, *Manufactured by Polar Electro Oy*, (2010) 11 pages.
Rainmaker, (Jun. 25, 2012, updated Feb. 16, 2013) "Garmin Swim watch in-Depth Review," [retrieved on Sep. 9, 2013 at http://www.dcrainmaker.com/2012/06/garmin-swim-in-depth-review.html, 38 pp.

* cited by examiner

USER IDENTIFICATION VIA MOTION AND HEARTBEAT WAVEFORM DATA

CROSS REFERENCE TO RELATED APPLICATIONS

This application is a continuation application of U.S. patent application Ser. No. 15/603,305, entitled: USER IDENTIFICATION VIA MOTION AND HEARTBEAT WAVEFORM DATA, filed May 23, 2017, which is a continuation application of U.S. patent application Ser. No. 15/231,627, entitled: USER IDENTIFICATION VIA MOTION AND HEARTBEAT WAVEFORM DATA, filed Aug. 8, 2016, which claims benefits under 35 U.S.C. § 119(e) to U.S. Provisional Patent Application No. 62/202,773, entitled USER IDENTIFICATION VIA COLLECTED FITNESS DATA, filed Aug. 7, 2015, the above prior applications being incorporated by reference in their entireties for all purposes.

BACKGROUND

Recent consumer interest in personal health has led to a variety of personal health monitoring devices being offered on the market. Recent advances in sensor, electronics, and power source miniaturization have allowed the size of fitness monitoring devices, also sometimes referred to as "biometric tracking devices," or "biometric monitoring devices," "wearable fitness monitors," "fitness monitors," etc. to be offered in small sizes that were previously impractical.

While such monitors have gained widespread acceptance and commercial success, the use of fitness data and other data obtained by such claims is still limited.

SUMMARY

Methods and systems are provided for determining the identification of a user of a wearable fitness monitors or authenticating the user of the wearable fitness monitors.

One aspect of the disclosure relates to methods for using two motion signatures to determine an identity of a wearer of a wearable fitness monitor. In some implementations, a method comprising: (a) obtaining a first motion signature obtained using data from one or more first motion sensors of a wearable fitness monitor configured to be worn by a person, wherein the first motion signature characterizes a movement experienced by the wearable fitness monitor; (b) obtaining a second motion signature obtained using data from one or more second motion sensors, wherein the second motion signature further characterizes the movement experienced by the wearable fitness monitor; (c) comparing the first and second motion signatures or a combination thereof to a reference motion feature for a user; and (d) based on the comparison in (c), determining whether an identity of a wearer of the fitness monitor is the user.

In some implementations, the one or more first motion sensors comprise an accelerometer, a gyroscope, a magnetometer, an altimeter, a GPS receiver, or any combination thereof. In some implementations, the one or more second motion sensors comprise one or more of the first motion sensors. In some implementations, the first motion signature is a time domain representation of a periodic motion of the movement experienced by the wearable fitness monitor. In some implementations, the periodic motion is produced by a movement of the wearer, wherein the movement is a step rate, a metric derived from an amplitude of the time domain representation, a biking cadence, a rowing rate, a resistance-based repetition rate, a typing speed, a zero crossing rate, a peak-to-peak time, an arm swing rate, and any combination thereof.

In some implementations, the first motion signature comprises a frequency domain representation of a periodic motion of the movement experienced by the wearable fitness monitor. In some implementations, the frequency domain representation of the periodic motion of the movement experienced by the wearable fitness monitor comprises a spectral component in the periodic motion. In some implementations, the spectral component is a harmonic in the frequency domain representation of the periodic motion. In some implementations, the first motion signature comprises a property of two or more harmonics in the frequency domain representation of the periodic motion.

In some implementations, the first motion signature comprises a motion periodicity and the second motion signature comprises a metric derived from an amplitude of the motion periodicity. In some implementations, the first motion signature comprises a time domain representation of a periodic motion and the second motion signature comprises a frequency domain representation of the periodic motion. In some implementations, the user's reference motion feature comprises a model of typical motion of the user. In some implementations, the user's reference motion feature is generated using data obtained from the one or more first motion sensors and the one or more second motion sensors when the user wears the wearable fitness monitor. In some implementations, the user's reference motion feature comprises a profile of a step by the user.

In some implementations, operation (c) of the method comprises comparing a combination of the first and second motion signatures to the user's reference motion feature, and wherein the user's reference motion feature comprises a line, a curve, or a look up table relating the first and second motion signatures for the user. In some implementations, (c) comprises (i) determining a difference between the user's reference motion feature and the first and second motion signatures or the combination thereof, and (ii) determining whether the difference is greater than a threshold. In some implementations, (c) comprises performing a linear discriminant analysis on the first and second motion signatures or the combination thereof with respect to the user's reference motion feature. In some implementations, (c) comprises determining that at least one of the first and second motion signatures is an invalid motion for a human wearer.

In some implementations, the method further comprises determining whether the first and second motion signatures, taken at the same time, represent the same activity or activity level of the user, wherein the one or more second motion sensors are located on a device that is separate from the wearable fitness monitor. In some implementations, the separate device is a mobile phone. In some implementations, determining whether the first and second motion signatures, taken at the same time, represent the same activity or activity level of the user comprises determining whether the first and second motion signatures represent a characteristic of a periodic motion. In some implementations, the first motion signature comprises a step count or a step rate and the second motion signature comprises a GPS or Bluetooth signature.

In some implementations of the methods above, at least one of the first and second motion signatures comprises a cycle profile of a periodic motion performed by the user, and wherein the reference motion feature is a predetermined typical cycle for the user's periodic motion. In some implementations, the cycle profile comprises a time varying amplitude of an output from the one or more first motion sensors. In some implementations, the user's periodic motion is selected from the group consisting of running, walking, cycling, swimming, weight lifting, climbing, rowing, a gymnastic exercise, dancing, an aerobic exercise, a yoga routine, golfing, swinging a club, swinging a racquet, striking a ball or another object, swimming, diving, surfing, skating, skiing, skate boarding, exercising on a machine, driving a vehicle, and riding an animal.

In some implementations, the method further includes repeating (a)-(d) at multiple times. In some implementations, wherein repeating (a)-(d) is performed automatically, without triggering by the wearer of the fitness monitor. In some implementations, the method further includes, responsive to determining that the identity of the wearer of the fitness monitor is not the user, preventing the wearable fitness monitor from allowing a transaction. In some implementations, the transaction comprises accessing a secure item or providing the user with an award for meeting an activity threshold.

In some implementations, the method further involves, responsive to determining that the identity of the wearer of the fitness monitor is not the user, requiring the user to authenticate himself or herself. In some implementations, requiring the user to authenticate comprises requiring the wearer of the fitness monitor to input a passcode, a fingerprint, an iris image, an ECG, a facial image, a vocal message, or any combination of the foregoing.

In some implementations, the method further involves, responsive to determining that the identity of the wearer of the fitness monitor is not the user, discrediting a fitness metric obtained for the user via the wearable fitness monitor.

In some implementations, the method further involves, responsive to determining that the identity of the wearer of the fitness monitor is the user, crediting a fitness metric obtained for the user via the wearable fitness monitor.

In some implementations, the method further involves, responsive to determining that the identity of the wearer of the fitness monitor is the user, allowing the wearable fitness monitor to facilitate a transaction. In some implementations, the transaction comprises accessing a secure item or providing the user with an award for meeting an activity threshold.

In some implementations, at least one of the one or more first motion sensors and the one or more second motion sensors are the same sensors.

In some implementations, (c) comprises obtaining a function between the first motion signature and the second motion signature, and comparing the function to a reference function based on the reference motion feature.

In some implementations, (c) comprises obtaining an average motion signature by averaging the first motion signature and the second motion signature, and comparing the average motion signature to the reference motion feature.

In some implementations, (c) comprises: extracting features from the first motion signature and the second motion signature; forming a feature vector using the extracted features, and applying a classifier to the feature vector to determine whether the feature vector belongs to a class corresponding to the reference motion feature.

In some implementations, the obtaining the first motion signature obtained using the data from the one or more first motion sensors comprises: low-pass filtering the data from the one or more first motion sensors; and obtaining a cycle profile from the low-pass filtered data. In some implementations, the obtaining the cycle profile from the low-pass filtered data comprises: obtaining local minima from the low-passed filtered data; dividing the low-passed filtered data into two or more segments using the local minima; and obtaining the cycle profile from the two or more segments. In some implementations, the obtaining the cycle profile from the two or more segments comprises: (i) rejecting one or more outliers among the two or more segments that deviate from the mean of the two or more segments. In some implementations, the obtaining the cycle profile from the two or more segments further comprises: repeating (i) one or more times among remaining segments. In some implementations, the obtaining the cycle profile from the two or more segments further comprises: averaging remaining segments to obtain the cycle profile.

In some implementations, the obtaining the first motion signature obtained using the data from the one or more first motion sensors further comprises: extracting one or more features from the cycle profile or values derived from the cycle profile. In some implementations, each feature is selected from the group consisting of: a slope, an inflection, a zero crossing, a derivative, a moment, a cumulant, and any combination thereof. In some implementations, comparing the first motion signature to the reference motion feature for the user comprises: obtaining a classifier using motion data obtained from the user; and applying the classifier to the extracted one or more features, wherein the classifier takes the one or more features as inputs and provides a classification of the wearer being the user or not the user as an output.

In some implementations, the classifier comprises a linear discriminant analysis classifier. In some implementations, the classifier comprises a neural network classifier. In some implementations, the classifier is trained using at least one cycle profile derived from motion data obtained from the user. In some implementations, the method further involves updating the classifier using additional motion data obtained from the user.

Another aspect of the disclosure relates to methods for using a motion signature and a heartbeat waveform signature or a body characteristic to determine an identity of a wearer of a wearable fitness monitor. In some implementations, a method involves: (a) obtaining a motion signature obtained using data from one or more motion sensors of a wearable fitness monitor configured to be worn by a person, wherein the motion signature characterizes a movement experienced by the wearable fitness monitor; (b) obtaining a heartbeat waveform signature obtained using data from one or more heartbeat waveform sensors, wherein the heartbeat waveform signature characterizes a detected heartbeat waveform of a wearer of the wearable fitness monitor; (c) comparing the motion signature and the heartbeat waveform signature or a combination thereof to one or more reference features of a user; and (d) based on the comparison in (c), determining whether an identity of the wearer of the fitness monitor is the user.

In some implementations, a method of identifying a user is provided. The method involves: (a) obtaining a motion signature obtained using data from one or more motion sensors of a wearable fitness monitor configured to be worn by a person, wherein the motion signature characterizes a movement experienced by the wearable fitness monitor; (b) obtaining a body characteristic obtained using data from one or more body characteristic sensors, wherein the body characteristic characterizes the body of a person wearing the wearable fitness monitor; (c) comparing the motion signature and the body characteristic or a combination thereof to at least one reference feature for a user; and (d) based on the comparison in (c), determining whether an identity of a wearer of the fitness monitor is the user.

In some implementations, the body characteristic is a detected response of the one or more body characteristic sensors to the wearer's skin. In some implementations, at least one of the one or more body characteristic sensors comprises a light pulse emitter and a light pulse detector configured to determine a variable response of the detector to a variable intensity of light pulses from the emitter.

In some implementations, the body characteristic is body composition determined through bioelectrical impedance. In some implementations, at least one of the one or more body characteristic sensors is disposed on the wearable fitness monitor.

A further aspect of the disclosure relates to methods for using a motion signature to determine an identity of a wearer of a wearable fitness monitor. In some implementations, a method includes: (a) obtaining a motion signature obtained using data from one or more motion sensors of a wearable fitness monitor configured to be worn by a person, wherein the motion signature characterizes a movement experienced by the wearable fitness monitor; (b) comparing the motion signature to a reference motion feature for a user; and (c) based on the comparison in (b), determining whether an identity of a wearer of the fitness monitor is the user. In some implementations, the motion signature characterizes a cycle of periodic movement of the person wearing the wearable fitness monitor.

In some implementations, the reference motion feature is a reference cycle for periodic movement of a user. In some implementations, the reference cycle is a predetermined typical cycle for the user's periodic motion. In some implementations, the motion signature comprises a time-varying amplitude of an output from the one or more motion sensors.

In some implementations, the user's periodic motion is selected from the group consisting of running, walking, cycling, swimming, weight lifting, climbing, rowing, a gymnastic exercise, dancing, an aerobic exercise, a yoga routine, golfing, swinging a club, swinging a racquet, striking a ball or another object, swimming, diving, surfing, skating, skiing, skate boarding, exercising on a machine, driving a vehicle, and riding an animal. In some implementations, the reference motion feature is a characteristic of a periodic motion. In some implementations, the reference motion feature is a metric derived from an amplitude.

In some implementations, the obtaining the motion signature obtained using the data from the one or more motion sensors comprises: low-pass filtering the data from the one or more motion sensors; and obtaining a cycle profile from the low-pass filtered data. In some implementations, the obtaining the cycle profile from the low-pass filtered data comprises: obtaining local minima from the low-passed filtered data; dividing the low-passed filtered data into two or more segments using the local minima; and obtaining the cycle profile from the two or more segments.

In some implementations, the obtaining the cycle profile from the two or more segments comprises: (i) rejecting one or more outliers among the two or more segments that deviate from the mean of the two or more segments. In some implementations, the obtaining the cycle profile from the two or more segments further comprises: repeating (i) one or more times among remaining segments. In some implementations, the obtaining the cycle profile from the two or more segments further comprises: averaging remaining segments to obtain the cycle profile.

In some implementations, the obtaining the motion signature obtained using the data from the one or more motion sensors further comprises: extracting one or more features from the cycle profile or values derived from the cycle profile. In some implementations, each feature is selected from the group consisting of: a slope, an inflection, a zero crossing, a derivative, a moment, a cumulant, and any combination thereof.

In some implementations, comparing the motion signature to the reference motion feature for the user comprises: obtaining a classifier using motion data obtained from the user; and applying the classifier to the extracted one or more features, wherein the classifier takes the one or more features as inputs and provides a classification of the wearer being the user or not the user as an output. In some implementations, the classifier comprises a linear discriminant analysis classifier.

An additional aspect of the disclosure relates to methods for using a motion signature to determine that the motion of a wearable fitness monitor is generated by non-human, and preventing a transaction based on the determination. In some implementations, a method includes: (a) obtaining a motion signature obtained using data from one or more motion sensors of a wearable fitness monitor configured to be worn by a person, wherein the motion signature characterizes a body movement of the person wearing the wearable fitness monitor; (b) determining whether the motion signature corresponds to an invalid motion feature, the invalid motion feature characterizing motion likely to be performed by a non-human; and (c) based on the determination in (b), preventing the wearable fitness monitor from allowing a transaction.

In some implementations, the transaction comprises accessing a secure item or providing an award for meeting an activity threshold to a user associated with the wearable fitness monitor. In some implementations, the method further involves, responsive to determining that the motion signature corresponds to the invalid motion feature, requiring a wearer of the fitness monitor to authenticate himself or herself. In some implementations, requiring the wearer to authenticate comprises requiring the wearer of the fitness monitor to input a passcode, a fingerprint, an iris image, an ECG, a facial image, a vocal message, or any combination of the foregoing.

In some implementations, determining whether the motion signature corresponds to an invalid motion feature in (b) comprises: obtaining an additional signature using data from one or more additional sensors, and determining that the motion signature, the additional signature, or a combination thereof is inconsistent with at least one human activity. In some implementations, the motion signature is step rate or step count and the additional signature is a heart rate or a heartbeat waveform.

In some implementations, determining whether the motion signature corresponds to the invalid motion feature in (b) comprises determining whether a periodicity for the motion signature is within a threshold periodicity for a given time period. In some implementations, the invalid motion feature is a periodic motion having a cycle-to-cycle consistency greater than a threshold. In some implementations, the invalid motion feature comprises one or more periodic motion contributions from one or more spatial dimensions that is less than a threshold.

Yet another aspect of the disclosure relates to methods for using a motion signature obtained from a wearable fitness monitor and an additional signature obtained from another device to determine if a wearer of the monitor is a particular user. In some implementations, a method involves: (a) obtaining a motion signature obtained using data from one or more motion sensors of a wearable fitness monitor configured to be worn by a user, wherein the motion signature characterizes a movement experienced by the wearable fitness monitor; (b) obtaining an additional signature obtained using the data from one or more additional sensors located on a device that is separate from the wearable fitness monitor, wherein the additional motion signature further characterizes the movement; (c) comparing the motion signature to the additional signature; and (d) based on the comparison in (c), determining whether an identity of a wearer of the fitness monitor is the user.

In some implementations, the motion signature and the additional signature are obtained from the data collected at the same time. In some implementations, the comparing in (c) comprises determining whether the motion signature and the additional signature represent the same activity or activity level of the user. In some implementations, determining whether the motion signature and the additional signature represent the same activity or activity level of the user comprises determining whether the motion signature and the additional signature represent a characteristic of the user's gait.

In some implementations, the separate device is a mobile phone. In some implementations, the motion signature comprises a step count or a step rate and the second motion signature comprises a GPS or Bluetooth signature.

Another aspect of the disclosure relates to systems and devices for implementing various methods described above. In some implementations, a system includes: (A) a wearable fitness monitor configured to be worn by a person and comprising: one or more first motion sensors, one or more second motion sensors, and a communication interface configured for communicating data from the one or more first motion sensors to a device external to the wearable fitness monitor; and (B) classification logic. The classification logic is configured to: (a) obtain a first motion signature obtained using data from one or more first motion sensors of a wearable fitness monitor configured to be worn by a person, wherein the first motion signature characterizes a movement experienced by the wearable fitness monitor; (b) obtain a second motion signature obtained using data from one or more second motion sensors, wherein the second motion signature further characterizes the movement experienced by the wearable fitness monitor; (c) compare the first and second motion signatures or a combination thereof to a reference motion feature for a user; and (d) based on the comparison in (c), determine whether an identity of a wearer of the fitness monitor is the user.

In some implementations, a system includes (A) a wearable fitness monitor configured to be worn by a person and comprising: one or more first motion sensors, one or more heartbeat waveform sensors, and a communication interface configured for communicating data from the one or more first motion sensors to a device external to the wearable fitness monitor; and (B) classification logic. The classification logic is configured to: (a) obtain a motion signature obtained using data from the one or more motion sensors, wherein the motion signature characterizes a movement experienced by the wearable fitness monitor, (b) obtain a heartbeat waveform signature obtained using data from the one or more heartbeat waveform sensors, wherein the heartbeat waveform signature characterizes a detected heartbeat waveform of a wearer of the wearable fitness monitor, (c) compare the motion signature and the heartbeat waveform signature or a combination thereof to one or more reference features of a user, and (d) based on the comparison in (c), determine whether an identity of the wearer of the fitness monitor is the user.

In some implementations, a system for identifying a user includes: (A) a wearable fitness monitor configured to be worn by a person and comprising: one or more first motion sensors, one or more body characteristic sensors, and a communication interface configured for communicating data from the one or more first motion sensors to a device external to the wearable fitness monitor; and (B) classification logic. The classification logic is configured to: (a) obtain a motion signature obtained using data from the one or more motion sensors, wherein the motion signature characterizes a movement experienced by the wearable fitness monitor, (b) obtain a body characteristic obtained using data from the one or more body characteristic sensors, wherein the body characteristic characterizes the body of a wearer of the wearable fitness monitor, (c) compare the motion signature and the body characteristic or a combination thereof to at least one reference feature for a user, and (d) based on the comparison in (c), determine whether an identity of the wearer of the wearable fitness monitor is the user.

In some implementations, a system includes: (A) a wearable fitness monitor configured to be worn by a person and comprising: one or more first motion sensors, and a communication interface configured for communicating data from the one or more first motion sensors to a device external to the wearable fitness monitor; and (B) classification logic configured to: (a) obtain a motion signature obtained using data from the one or more motion sensors, wherein the motion signature characterizes a movement experienced by the wearable fitness monitor, (b) compare the motion signature to a reference motion feature for a user, and (c) based on the comparison in (b), determine whether an identity of a wearer of the fitness monitor is the user.

In some implementations, a system includes: (A) a wearable fitness monitor configured to be worn by a person and comprising: one or more first motion sensors, and a communication interface configured for communicating data from the one or more first motion sensors to a device external to the wearable fitness monitor; and (B) classification logic configured to: (a) obtain a motion signature obtained using data from the one or more motion sensors, wherein the motion signature characterizes a body movement of a wearer of the wearable fitness monitor, (b) comparing the motion signature to an invalid motion feature, the invalid motion feature characterizing motion likely to be performed by a non-human; and (c) based on the determination in (b), prevent the wearable fitness monitor from allowing a transaction.

In some implementations, a system includes: a wearable fitness monitor configured to be worn by a user and comprising: one or more first motion sensors, and a communication interface configured for communicating data from the one or more first motion sensors to a device external to the wearable fitness monitor; one or more additional sensors located on a device that is separate from the wearable fitness monitor; and classification logic. The classification logic is configured to: (a) obtain a motion signature obtained using data from the one or more first motion sensors, wherein the motion signature characterizes a movement experienced by the wearable fitness monitor; (b) obtain an additional signature obtained using data from the one or more additional sensors, wherein the additional motion signature further characterizes the movement; (c) compare the motion signature to the additional signature; and (d) based on the comparison in (c), determine whether an identity of a wearer of the fitness monitor is the user.

These and other objects and features of the present disclosure will become more fully apparent from the following description and appended claims, or may be learned by the practice of the disclosure as set forth hereinafter.

BRIEF DESCRIPTION OF THE DRAWINGS

The various implementations disclosed herein are illustrated by way of example, and not by way of limitation, in the figures of the accompanying drawings, in which like reference numerals may refer to similar elements.

DETAILED DESCRIPTION

Figure 1:
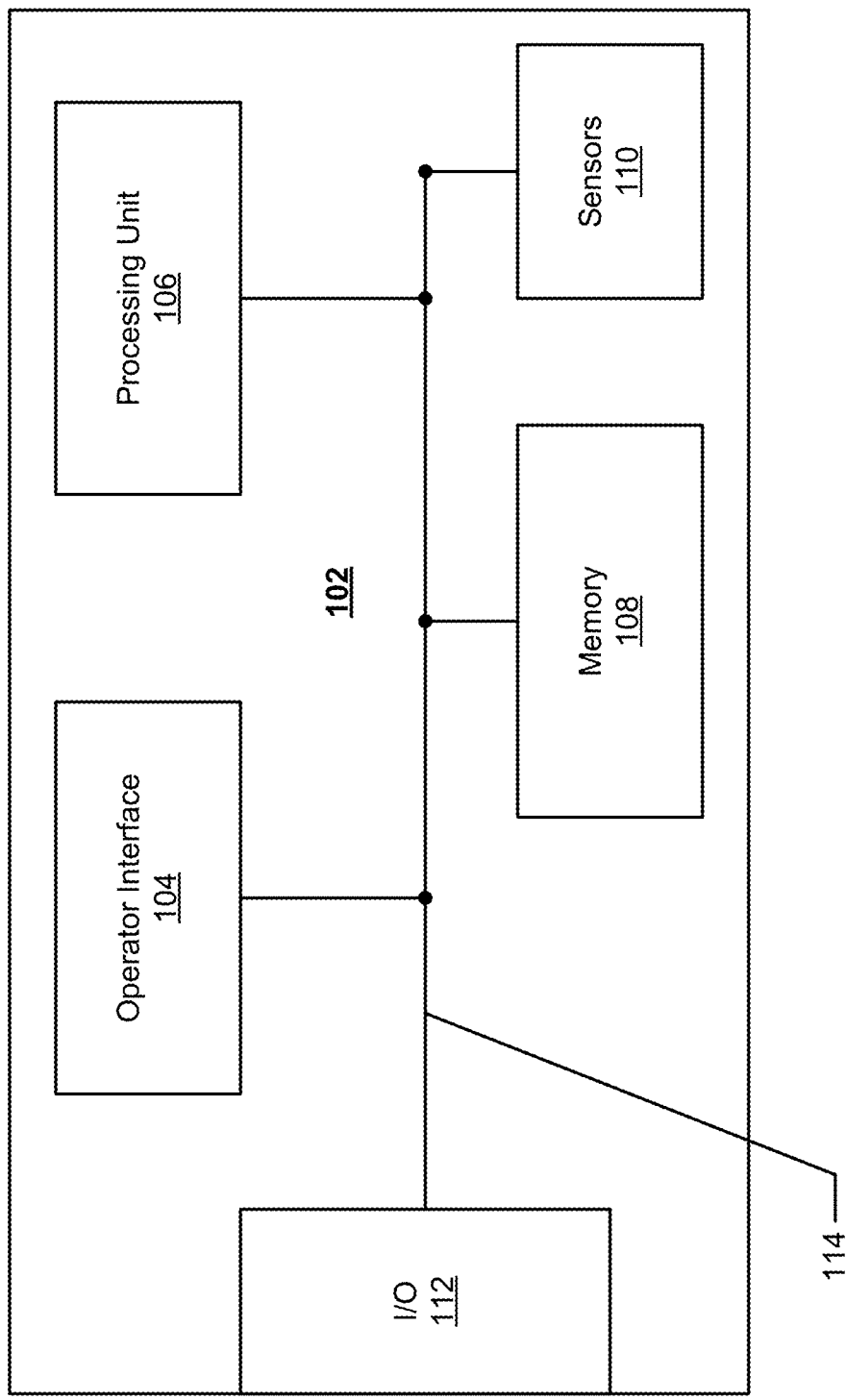
FIG. 1 depicts a generalized schematic of an example wearable fitness monitor with which various operations described herein may be executed.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

Context and Overview

This disclosure relates to methods, devices, and systems to recognize a user of a wearable fitness monitor using information obtained using the wearable fitness monitor.

Example Contexts which May Identify Users Via Wearable Fitness Monitors

In cases where a wearable fitness monitor is shared amongst several users, the wearable fitness monitor can provide data to the correct user's digital account.

When used to access secure resources, it may be useful for some embodiments that the wearable fitness monitor can estimate the identity of the user with some amount of certainty.

When data from the wearable fitness monitor is used to provide monetary incentives for user behavior, it may be useful for some embodiments that the wearable fitness monitor knows the identity of the user with some certainty. Additionally, trust of the user data itself (e.g., that a "step" is a true user step rather than a fake motion, hereinafter referred to as a "fake") can be an important aspect to some embodiments.

When data from the wearable fitness monitor is used to compete with other users of wearable fitness monitors, the veracity of the data and the identity of the user can be an important feature to verify, which can ensure that the data used to compete is not faked.

Overview

In one aspect, this disclosure presents a method including the following operations: (a) obtaining a first motion signature obtained using data from one or more first motion sensors of a wearable fitness monitor configured to be worn by a person, wherein the first motion signature characterizes a movement experienced by the wearable fitness monitor; (b) obtaining a second motion signature obtained using the data from one or more second motion sensors, wherein the second motion signature further characterizes the movement experienced by the wearable fitness monitor; (c) comparing the first and second motion signatures or a combination thereof to a reference motion feature for a user; and (d) based on the comparison in (c), determining whether an identity of a wearer of the fitness monitor is the user. In some embodiments, the one or more first motion sensors include an accelerometer, a gyroscope, a magnetometer, an altimeter, a GPS receiver, or any combination thereof.

A "combination" of motion signatures in (c) may be used in cases where the signatures are not analyzed separately, but together as in the case of a point or a curve in a multi-dimensional signature space. In other embodiments, each of the first and second signatures is separately compared against the reference motion signature.

In certain embodiments, the "movement" experienced by the wearable fitness monitor is a voluntary body movement such as the wearer's intentional movement of her head, neck, eyelid, mouth, shoulder, arm, wrist, finger, torso, hips, knee, ankle, and/or toe. In various implementations, the movement is characterized by a wearer's gait or stride when walking or running. The movement may be associated with a particular activity type such as running, walking, cycling, swimming, weight lifting, climbing, rowing, a gymnastic exercise, dancing, an aerobic exercise, a yoga routine, golfing, swinging a club, swinging a racquet, striking a ball or another object, swimming, diving, surfing, skating, skiing, skate boarding, exercising on a machine, driving a vehicle, riding an animal, etc. In some cases, the movement does not include involuntary motions such as heartbeats which may be determined using, e.g., sensor technology include photoplethysmography (PPG), electrocardiography (ECG), etc.

The comparison of the signature(s) and the reference motion signature may indicate that the wearer is not the user. Such cases may arise where the wearer is a different individual than the user and cases where the "wearer" is a robot or other automaton. The "reference motion feature" used in operation (c) may be a user reference motion feature (a template built using historical motion data of the user).

It should be understood that determining whether an identity of the wearer of the fitness monitor is the user may be a matter of probability or a prediction of whether the user is likely wearing the monitor. As explained elsewhere herein, the determination may be made by mathematical or other logical techniques that determine a distance or difference between the wearer's current motion signature(s) and the user's reference motion feature in movement signature space. As such, the determination may rely on a classification technique which provides a likelihood, rather than certainty, that the wearer is the user. For instance, classifiers using one or more of the following techniques may be used to determine the likelihood that the wearer is the user: linear discriminant analysis, neural network, clustering techniques, support vector machine, logistic regression, naive Bayes, random forest, decision tree, etc.

The sensor producing the data for the first and second motion signatures may be the same or different or they may overlap, with some first motion sensors being the same as some second motion sensors. In certain embodiments, the one or more second motion sensors include at least one motion sensor from the one or more first motion sensors.

In certain embodiments, the first motion signature is a time domain representation of a periodic motion of the movement experienced by the wearable fitness monitor, which periodic motion may be a person's gait, which may be, for example, a step rate, a metric derived from an amplitude of the wearer's periodic motion, a biking cadence, a rowing rate, a resistance-based repetition rate (for, e.g., weightlifting), a typing speed, a zero-crossing rate, a peak-to-peak time, an arm swing rate, or a combination thereof. In certain embodiments, the first motion signature is a frequency domain representation of a person's periodic motion (e.g., gait), which may include, for example, contributions of a spectral component (e.g., the fundamental frequency or a harmonic thereof) in the first motion signature. In some examples, the spectral component includes a combination of the harmonics or the fundamental frequency and one or more harmonics. As an example, a combination of the contributions of harmonics may be a property of two or more harmonics (or the fundamental frequency) such as a ratio of the powers of the individual harmonics.

Various combinations of the first and second motion signatures may be used. For example, the first motion signature includes a motion periodicity parameter (e.g., step rate) and the second motion signature includes a metric derived from an amplitude of the wearer's periodic motion. In another example, the first motion signature includes a time domain representation of a periodic motion (e.g., a wearer's gait) and the second motion signature includes a frequency domain representation of the periodic motion.

The user's reference motion feature typically has characteristics that facilitate comparison with the motion signatures. For example, the user's reference motion feature may include a predetermined typical motion signature for the user. Such feature may be obtained in various ways such as by using data obtained from the one or more first motion sensors and the one or more second motion sensors when the user wears the wearable fitness monitor. In such cases, it should be established that the user is actually wearing a fitness monitor when capturing data for generating her reference motion feature. In certain embodiments, the user's reference motion feature comprises a profile of a step by the user.

In some implementations, comparing the motion signature(s) to the user's reference motion feature in (c) includes comparing a combination of the first and second motion signatures to the user's reference motion feature. In such implementations, the user's reference motion feature may be a relationship between the first and second motion signatures for the user. As examples, the relationship may be a line, a curve, a look up table, etc. relating the first and second motion signatures for the user. In some examples, comparing the motion signature(s) to the reference motion feature includes (i) determining a distance (or difference) between the user's reference motion feature and the first and second motion signatures or the combination thereof, and (ii) determining whether the distance (or difference) is greater than a threshold. As explained elsewhere, the distance is a minimum separation between two points, lines, surfaces, etc. in multidimensional analysis. It may be viewed as a type of "difference."

In some implementations, the comparison in (c) includes performing a linear discriminant analysis (LDA) on the first and second motion signatures or the combination thereof with respect to the user's reference motion feature. The operations and applications of LDA are further explained hereinafter.

In certain embodiments, the comparison in (c) includes determining that at least one of the first and second motion signatures is an invalid motion for a human user (e.g., it is unnatural for a human user). As an example, a machine provides movements from which the fitness monitor generates data having unnaturally high consistency over time or from cycle to cycle. Also, data produced from machine movements may be unnaturally limited to contributions from one or a few axes (e.g., one axis of a three-axis accelerometer or gyroscope). In various implementations, the comparison between motion signatures and a reference motion feature may be performed by various classification techniques such as LDA, neural network, clustering, logistic regression, support vector machine, naïve Bayes, etc. In some embodiments, the method includes an operation of determining whether the first and second motion signatures, taken at the same time, represent the same activity or activity level of the user. In some implementations, determining whether the first and second motion signatures, taken at the same time, represent the same activity or activity level of the user includes determining whether the first and second motion signatures represent a characteristic of a periodic motion. For example, the motion signatures may be compared to determine whether they represent the same gait of a wearer. As an example, the first motion signature includes a step count or a step rate and the second motion signature includes a GPS or Bluetooth signature. This approach may be particularly relevant where the one or more second motion sensors are located on a device that is separate from the wearable fitness monitor, such as a smart phone or a second monitoring device worn or carried by the wearer of the fitness monitor. In some examples, the separate device is a mobile phone or other portable device with one or more sensors.

The motion signatures may be or include representations of multiple cycles of the wearer's movement or even a single cycle. For example, at least one of the first and second motion signatures may include a cycle profile of a periodic motion performed by the user. In such cases, the reference motion feature may be a predetermined typical cycle for the user's periodic motion. In some implementations, the cycle profile is a time varying amplitude of an output from the one or more first motion sensors. In some implementations, the user's periodic motion is running, walking, cycling, swimming, weight lifting, climbing, rowing, a gymnastic exercise, dancing, an aerobic exercise, a yoga routine, golfing, swinging a club, swinging a racquet, striking a ball or another object, swimming, diving, surfing, skating, skiing, skate boarding, exercising on a machine, driving a vehicle, riding an animal, etc.

In some cases, the process of obtaining the wearer's motion signatures and comparing them with the user's reference motion feature is performed repeatedly, sometime continuously. For example, the above method may involve repeating operations (a)-(d) at multiple times. The repeating of operations (a)-(d) may be performed automatically, without triggering by the wearer of the fitness monitor.

Determining whether or not the wearer of the fitness monitor is the user can be used in various contexts, often in the same or similar way as biometric information is conventionally used. When the system/method determines that the wearer is not the user, various actions may be taken to block a transaction involving the wearer, require the wearer to take additional steps to authenticate or otherwise identify herself, etc. In some cases, responsive to determining that the identity of the wearer of the fitness monitor is not the user, the method prevents the wearable fitness monitor from allowing a transaction. As examples, the transaction may be accessing a secure item or providing the user with an award for meeting an activity threshold, which may be determined from quantifiable biometric information. In certain embodiments, responsive to determining that the identity of the wearer of the fitness monitor is not the user, the method requires the user to authenticate himself or herself. As examples, requiring the user to authenticate may include requiring the wearer of the fitness monitor to input a passcode, a fingerprint, an iris image, an ECG, a facial image, a vocal message, or any combination of the foregoing. In certain embodiments, responsive to determining that the identity of the wearer of the fitness monitor is not the user, the method discredits a fitness metric obtained for the user via the wearable fitness monitor.

When the system/method determines that the wearer is the user, various actions may be taken to credit the user or allow the user to engage in a transaction. In certain embodiments, responsive to determining that the identity of the wearer of the fitness monitor is the user, the method credits a fitness metric obtained for the user via the wearable fitness monitor. In certain embodiments, responsive to determining that the identity of the wearer of the fitness monitor is the user, the method allows the wearable fitness monitor to facilitate a transaction. Examples of such transactions include accessing a secure item or providing the user with an award for meeting an activity threshold.

In certain embodiments, at least one of the one or more first motion sensors and the one or more second motion sensors are the same sensors. In certain embodiments, the data from the first and second motions sensors includes at least a first datum from the one or more first motion sensors and a second datum from the one more second motion sensors.

Another aspect of the disclosure pertains to methods including the following operations: (a) obtaining a motion signature obtained using data from one or more motion sensors of a wearable fitness monitor configured to be worn by a person, wherein the motion signature characterizes a movement experienced by the wearable fitness monitor; (b) obtaining a heartbeat waveform signature obtained using data from one or more heartbeat waveform sensors, wherein the heartbeat waveform signature characterizes a detected heartbeat waveform of a wearer of the wearable fitness monitor; (c) comparing the motion signature and the heartbeat waveform signature or a combination thereof to one or more reference features of a user; and (d) based on the comparison in (c), determining whether an identity of the wearer of the fitness monitor is the user. In certain contexts, a wearer is a non-human wearer and, in certain cases, a "heartbeat waveform" is detected where the non-human lacks a heartbeat. The method may be employed to identify the user, deauthenticate the user, etc. as described above.

Another aspect of the disclosure pertains to methods including the following operations: (a) obtaining a motion signature obtained using data from one or more motion sensors of a wearable fitness monitor configured to be worn by a person, wherein the motion signature characterizes a movement experienced by the wearable fitness monitor; (b) obtaining a body characteristic obtained using data from one or more body characteristic sensors, wherein the body characteristic characterizes the body of a person wearing the wearable fitness monitor; (c) comparing the motion signature and the body characteristic or a combination thereof to at least one reference feature for a user; and (d) based on the comparison in (c), determining whether an identity of a wearer of the fitness monitor is the user. The method may be employed to identify the user, deauthenticate the user, etc. as described above.

Various types of body characteristic may be employed, some related to body morphology, some to body composition, some to body color, etc. In certain embodiments, the body characteristic is one or more characteristics of the wearer's skin (e.g., the wearer's skin color). Skin color or another skin characteristic can be determined (or approximated) by various techniques. In one implementation, at least one of the one or more body characteristic sensors includes a light pulse emitter and a light pulse detector configured to determine a variable response of the detector to a intensity of light pulses from the emitter. The variability of the response of the detector is can be influenced by the user's skin color. Thus, this response may be used as a signature that is compared against a reference feature of a user. In certain embodiments, the body characteristic is body composition determined through bioelectrical impedance. In some implementations, at least one of the one or more body characteristic sensors is disposed on the wearable fitness monitor.

Another aspect of the disclosure pertains to methods including the following operations: (a) obtaining a motion signature obtained using data from one or more motion sensors of a wearable fitness monitor configured to be worn by a person, where the motion signature characterizes a movement experienced by the wearable fitness monitor; (b)

comparing the motion signature to a reference motion feature for a user; and (c) based on the comparison in (b), determining whether an identity of a wearer of the fitness monitor is the user. In some implementations, data from the one or more motion sensors are preprocessed before the motion signature is obtained. In some implementations the reference motion feature may be updated continuously or periodically after the identity of the wearer has been determined. In some implementations, the comparison in operation (b) is implemented using an LDA classifier.

In some embodiments, the motion signature characterizes a cycle of periodic movement of the person wearing the wearable fitness monitor. A cycle contains information about a wearer's step or other unit of periodic motion. Examples of the user's periodic motion include running, walking, cycling, swimming, weight lifting, climbing, rowing, a gymnastic exercise, dancing, an aerobic exercise, a yoga routine, golfing, swinging a club, swinging a racquet, striking a ball or another object, swimming, diving, surfing, skating, skiing, skate boarding, exercising on a machine, driving a vehicle, riding an animal, etc. In certain embodiments, a motion signature for a cycle includes a time-varying amplitude of an output from the one or more motion sensors. The motion signature for a cycle may be obtained for data generated during a single instance of the cycle or from multiple instances, with the instances being averaged or otherwise combined to provide the "cycle" used in this method. In embodiments where the motion signature is a cycle, the reference motion feature may be a reference cycle for periodic movement of a user. In some cases, such reference cycle is a predetermined typical cycle for the user's periodic motion. The method may be employed to identify the user, deauthenticate the user, etc. as described above. In certain embodiments, the reference motion feature is a characteristic of a periodic motion. In certain embodiments, the reference motion feature is a metric derived from an amplitude (e.g., an amplitude a reference cycle).

Another aspect of the disclosure pertains to methods including the following operations: (a) obtaining a motion signature obtained using data from one or more motion sensors of a wearable fitness monitor configured to be worn by a person, where the motion signature characterizes a body movement of the person wearing the wearable fitness monitor; (b) determining whether the motion signature corresponds to an invalid motion feature, the invalid motion feature characterizing motion likely to be performed by a non-human; and (c) based on the determination in (b), preventing the wearable fitness monitor from allowing a transaction (or deauthenticating a user associated with the fitness monitor). In certain embodiments, the transaction includes accessing a secure item or providing an award for meeting an activity threshold to a user associated with the wearable fitness monitor. In some implementations, the invalid motion feature is simply an unnatural (for humans or non-machines) level of consistency or repetition in the motion signature. In a further example, an invalid motion feature has limited dimensional range; for example, the motion feature unnaturally (for a human or non-machine) emphasizes one or two spacial dimensions. The user identification logic can identify this level of consistency or limited dimensional range by comparing the relevant motion signature component to a defined threshold.

As mentioned unnatural motion signatures might be generated by automatons or other machines. Additionally, an unnatural motion signature may be generated by a non-human animal wearing the fitness monitor. In certain embodiments, an approach as described here allows a system or entity to deauthenticate a user, discredit a user, prevent access to a secure item, and/or prevent a transaction involving the user. For example, in certain embodiments, responsive to determining that the motion signature corresponds to an invalid motion feature, the method requires a wearer of the fitness monitor to authenticate himself or herself. In some implementations, requiring the wearer to authenticate includes requiring the wearer of the fitness monitor to input a passcode, a fingerprint, an iris image, an ECG, a facial image, a vocal message, or any combination of the foregoing. In certain embodiments, operation (c) includes determining that the motion signature matches an invalid motion feature, the invalid motion feature characterizing motion likely to be performed by a non-human.

In certain embodiments, determining whether the motion signature corresponds to an invalid motion feature in (b) includes obtaining an additional signature using data from one or more additional sensors, and determining that the motion signature and/or the additional signature are/is inconsistent with a human activity. In one example, the motion signature is step rate or step count and the additional signature is a heart rate or a heartbeat waveform. In certain embodiments, determining whether the motion signature corresponds to the invalid motion feature in (b) includes determining whether a periodicity for the motion signature is within a threshold periodicity for a given time period. In some in some embodiments, determining whether the motion signature corresponds to the invalid motion feature in (b) includes determining a relation (e.g., a function) between step rate and heart rate for human activities, and determining that a combination of the motion signature (e.g., measured step rate) and the additional signature (e.g., measured heart rate) is inconsistent with the relation determined for one or more human activities. In some implementations, a measured step rate is compared to a reference step rate range associated with human activities to determine whether the measure step rate is outside of the step rate range of human activities. In some implementations, measured heart rate is compared to a heart rate range of human activities to determine whether the measured heart rate is outside of the heart rate range of human activities.

Another aspect of the disclosure concerns a method including the following operations: (a) obtaining a motion signature obtained using data from one or more motion sensors of a wearable fitness monitor configured to be worn by a person, wherein the motion signature characterizes a movement experienced by the wearable fitness monitor; (b) obtaining an additional signature obtained using data from one or more additional sensors located on a device that is separate from the wearable fitness monitor, wherein the additional motion signature further characterizes the movement experienced by the wearable fitness monitor, or characterizes movement experienced by the device that is separate from the wearable fitness monitor; (c) comparing the motion signature to the additional signature; and (d) based on the comparison in (c), determining whether an identity of a wearer of the fitness monitor is the user.

In certain embodiments, the motion signature and the additional signature are obtained from the data collected at the same time. In some implementations, the comparing in (c) includes determining whether the motion signature and the additional signature represent the same activity or activity level of the user. In some implementations, determining whether the motion signature and the additional signature represent the same activity or activity level of the user comprises determining whether the motion signature and the additional signature represent a characteristic of the user's gait. As an example, the separate device is a mobile phone, a second fitness monitor, a headset, or other portable device. In some cases, the motion signature includes a step count or a step rate and the second motion signature includes a GPS or Bluetooth signature.

One aspect of the disclosure relates to systems that use sensor data to verify the identity of a wearer of a wearable fitness monitor. In various implementations, the sensor data include data from one or more motion sensors of the wearable fitness monitor. Various implementations of the systems are configured to perform any of the methods described above.

In some implementations, the system includes a wearable fitness monitor configured to be worn by a person. The wearable fitness monitor includes one or more first motion sensors, one or more second motion sensors, and a communication interface configured for communicating data from the one or more first motion sensors to a device external to the wearable fitness monitor. The system also includes classification logic configured to perform operations to implement one or more methods described above. For example, in one implementation, the classification logic is configured to: (a) obtain a first motion signature obtained using data from the one or more first motion sensors of the wearable fitness monitor, wherein the first motion signature characterizes a movement experienced by the wearable fitness monitor, (b) obtain a second motion signature obtained using the data from the one or more second motion sensors, wherein the second motion signature further characterizes the movement experienced by the wearable fitness monitor, (c) compare the first and second motion signatures or a combination thereof to a reference motion feature for a user, and (d) based on the comparison in (c), determine whether an identity of a wearer of the fitness monitor is the user.

In other implementations, the wearable fitness monitor is configured to be worn by a person and includes: one or more first motion sensors, and a communication interface configured for communicating data from the one or more first motion sensors to a device external to the wearable fitness monitor. In some implementations, the wearable fitness monitor also includes one or more heartbeat waveform sensors. In other implementations, the wearable fitness monitor also includes one or more body characteristic sensors.

In further implementations, the wearable fitness monitor includes: one or more first motion sensors, one or more body characteristic sensors, and a communication interface configured for communicating data from the one or more first motion sensors to a device external to the wearable fitness monitor.

In some implementations, the system includes (a) a wearable fitness monitor configured to be worn by a person. The wearable fitness monitor includes: one or more first motion sensors, and a communication interface configured for communicating data from the one or more first motion sensors to a device external to the wearable fitness monitor. The system also includes (b) classification logic, and (c) one or more sensors located on a device that is separate from the wearable fitness monitor.

User Identification from Motion Signatures

As explained, the methods and systems described herein identify users of fitness monitors that produce data from a motion sensor that responds to the user's movements (e.g., motion of a limb, head, torso, wrist, etc.). Such voluntary movements are typically produced for purposes other than user identification or authentication, typically for the purpose of activity tracking and monitoring. They may be generated from the user's normal walking or fitness activities.

Motion signatures may include any data relating motion periodicity (otherwise referred to as periodic motion) obtained from the motion sensor are analyzed by, e.g., classification logic to determine whether the detected motions are those of the user. Examples of data relating to motion periodicity include step rate, a metric derived from the amplitude of the motion signal, a biking cadence, a rowing rate, a resistance-based repetition rate (e.g., weightlifting repetition rates), a typing speed, a zero crossing rate, a peak-to-peak time, an arm swing rate, or a combination thereof. A metric derived from the amplitude of the motion signal may be referred to herein as "motion signal energy." Motion energy may be calculated through various methods, such as classical energy formulas as well as simplified calculations, such as finding the absolute difference of motion signals.

One or more motion signatures may be used to identify a user. When multiple motion signatures are used, they may be used separately or in combination to identify a user. One example of a combination is a line or curve relating two or more signature types for a user. For example, a user's motion signal energy may vary as a function of step rate in a reproducible manner. Another example of a combination is where the values of multiple motion signatures are hashed or otherwise used to index a lookup table. In some cases, sensors other than motion sensors in the wearable fitness monitor are used to help identify the user wearing the fitness monitor. Such other sensors include heartbeat waveform sensors (PPG sensors and ECG sensors), bioimpedance sensors, and EEGs, the like. In some cases, such sensors measure involuntary body motions such a heart beats and respiration. An example of combination of a motion signature and another signature is a relationship between heartrate and step rate for a user.

A positive or negative identification of a user may be applied in various contexts such as insurance (e.g., an insured's fitness level factors into her premium), automatically switching users sharing a wearable fitness device, accessing secure devices such as automobile ignition systems, door locks, media systems, etc., and fitness competitions where the method credits or discredits the user's fitness results.

Timing and Use of User Identification from the Wearable Fitness Monitor (Use Cases)

Identifying a user as described herein may be performed at various times and frequencies. In some cases, the identifying is performed at a time when she needs to enter into a transaction such as accessing a secure device. For example, the system may evaluate a current motion signature from a wearable fitness monitor to confirm that a user can execute a transaction (such as accessing a secure device, or receiving an insurance benefit) at the time when the user wants to execute the transaction. Such can occur when the activity tracker detects an interaction with a payment system, as may occur via an NFC protocol, a Bluetooth connection, or a triggering event initiated by an application executing on the activity tracker.

In some implementations, a user who wears a fitness monitor regularly over a period of days, weeks, months, years, etc. may have her identity checked periodically, with or without notifying the user. The classification logic may check the identity of the wearer of the fitness monitor automatically, without prompting from the user. Changes in status may occur with or without notifying the user, e.g., user identification logic may determine that a fitness monitor that was identified as being worn by the user is no longer being worn by the user. Or the classification logic may determine that it can no longer conclude with a requisite level of confidence that the monitor is being worn by the user. Such checks and adjustments may be made in the "background," that is to say that they are performed without the user's input and/or without notifying the user.

In some implementations, evaluating motion signatures from a wearable fitness monitor results in deauthenticating a previously authenticated wearable fitness monitor and blocks execution of a transaction. In one sequence, the process or classification logic starts by authenticating a user by using a technique other than a continuous or quasi-continuous fitness tracking measurement based on gait, heartbeat waveform, etc. Examples of the initial authentication techniques include fingerprint capture, ECG measurement, personal identification number (PIN) entry, and/or bioimpedance measurement. Such techniques often require only a short duration (e.g., a minute or less) to authenticate a user. After the classification logic authenticates the user, the wearable fitness monitor motion signatures are continually or periodically evaluated by the classification logic to determine whether to maintain authentication or deauthenticate the user/device. Such evaluations may be conducted in the background by the classification logic during normal operation of the wearable fitness monitor. When the classification logic determines that the user is authenticated or deauthenticated, it may or may not notify user. In some embodiments, the user is not notified until she attempts to execute a transaction.

In some cases, the user identification logic initially authenticates the user using the short duration technique (e.g., fingerprint, ECG, bioimpedance, etc.), and the logic then acquires the motion signatures produced by the voluntary and/or involuntary actions of the user wearing the fitness monitor, and uses these motion signatures to train a profile or other relationship between the motion signatures and a specific user.

In some cases, the device or logic may prompt the user to re-authenticate by verifying a code provided by a trusted device (e.g., a mobile phone in which authentication is achieved via fingerprint or PIN code) or any of the motion, heartbeat, or other fitness monitor-based authentication methods described in this disclosure. Prompting may occur by a vibration or haptic interaction from the wearable fitness monitor. Prompting may occur at the next moment in which the wearable fitness monitor's user interface is engaged (e.g., upon pressing a button or providing a motion gesture such as moving a wrist wearable toward the face).

Wearable Fitness Monitors—Structure and Operation

Wearable fitness monitors suitable for use with the methods and systems described herein collect data for the user of the device such as activity, sleep, and physiological measures. Examples include steps, distance traveled, calories burned, pace, floors climbed, elevation, number of active minutes, the start and stop of a sleep period, the duration of sleep, the number of awakenings during sleep, sleep disturbances from external stimuli, sleep stages, apnea hypopnea index, heart rate, resting heart rate, maximum heart rate, heart rate variability, time spent in at a specific exertion level (e.g., "cardio" zone), blood pressure, arterial stiffness, cardiovascular fitness, blood glucose, stress and/or relaxation levels, power output on a bicycle, number of swimming laps in a pool, number of swimming strokes, type of swimming strokes, lap splits, running mile splits, path walked or run overland (e.g., via GNSS tracking), location, time spent at work, home or the gym, number and/or length of sedentary periods in a day, start and stop of exercise activities such as walking, running, elliptical, swimming, bicycling, cardio workout, VO2max, SpO2, proximity to and interactions with other wearable fitness monitor users, risk of arrhythmia, lactate threshold, hydration level, water loss during an exercise, body fat, number of reps, sets, and types of exercises performed in a resistance training session, yoga poses performed and duration, respiration rate, etc., etc. Please note that "wearable fitness monitors" used herein may be a standalone wearable fitness monitor, multiple wearable fitness monitors, or one or more wearable fitness monitors in communication with an external server(s) used together to track user activity.

Wearable fitness monitors are devices that are worn on or carried by a person. They come in many form factors: wrist band, watch, clip, shoe pod, shoe, pendant, earbuds, clothing (shirt, socks, pants, undergarments), belt, cuff links, glasses, ring, earring (nose ring, studs, etc.), helmet, hat, hair clip, and socks. For the sake of simplicity, a handheld mobile phone will also be classified as a wearable fitness monitor because it is either held by or worn on the person for significant periods.

In some implementations, a set of protective, attachable and/or wearable cases (herein referred to simply as "cases") that enable a user to wear a single wearable fitness monitor in multiple fashions or body locations may be provided. For example, in some implementations, a wearable fitness monitor may be designed such that it may be inserted into, and removed from, a plurality of compatible cases. In other implementations, the wearable fitness monitors may be permanently or semi-permanently mounted into (or joined to) straps, clips, clasps, bands, or other attachments for wear. Generally speaking, the various individual elements of the various example cases and/or biometric tracking devices shown herein may also be combined with elements from other example cases and/or biometric tracking devices shown herein, e.g., a necklace or pendant case for a removable wearable fitness monitor may also be provided for a permanently-mounted wearable fitness monitor. Such combinations of elements are considered to be within the scope of this disclosure. Generally speaking, a wearable fitness monitor or biometric tracking device combined with a case or some other means allowing it to be worn or easily carried by a person may be referred to herein as a "biometric monitoring system" or "biometric tracking system."

FIG. 1 depicts a generalized schematic of an example wearable fitness monitor or other device with which the various operations described herein may be executed. The wearable fitness monitor 102 may include a processing unit 106 having one or more processors, a memory 108, an operator interface 104, one or more biometric sensors 110, and input/output 112. The processing unit 106, the memory 108, the operator interface 104, the one or more biometric sensors 110, and the input/output 112 may be communicatively connected via communications path(s) 114 (it is to be understood that some of these components may also be connected with one another indirectly).

The wearable fitness monitor (also referred to herein as "the device") may collect one or more types of biometric data, e.g., data pertaining to physical characteristics of the human body (such as heartbeat, perspiration levels, etc.) and/or data relating to the physical interaction of that body with the environment (such as accelerometer readings, gyroscope readings, etc.), from the one or more biometric sensors 110 and/or external devices (such as an external heart rate monitor, e.g., a chest-strap heart rate monitor) and may then store such information for later use, e.g., for communication to another device via the I/O 112, e.g., a smartphone or to a server over a wide-area network such as the Internet. The processing unit 106 may also perform an analysis on the stored data and may initiate various actions depending on the analysis. For example, the processing unit 106 may determine that the data stored in the memory 108 indicates that a goal threshold has been reached and may then display content on a display of the portable biometric tracking device celebrating the achievement of the goal. The display may be part of the operator interface 104 (as may be a button or other control, not pictured, that may be used to control a functional aspect of the wearable fitness monitor).

In general, a wearable fitness monitor may incorporate one or more types of user interfaces including but not limited to visual, auditory, touch/vibration, or combinations thereof. The wearable fitness monitor may, for example, display the state of one or more of the data types available and/or being tracked by the wearable fitness monitor through, for example, a graphical display or through the intensity and/or color of one or more LEDs. The user interface may also be used to display data from other devices or internet sources. The device may also provide haptic feedback through, for instance, the vibration of a motor or a change in texture or shape of the device. In some implementations, the biometric sensors themselves may be used as part of the user interface, e.g., accelerometer sensors may be used to detect when a person taps the housing of the biometric monitoring unit with a finger or other object and may then interpret such data as a user input for the purposes of controlling the wearable fitness monitor. For example, double-tapping the housing of the wearable fitness monitor may be recognized by the wearable fitness monitor as a user input that will cause the display of the wearable fitness monitor to turn on from an off state or that will cause the wearable fitness monitor to transition between different monitoring states, e.g., from a state where the wearable fitness monitor may interpret data according to rules established for an "active" person to a state where the wearable fitness monitor may interpret data according to rules established for a "sleeping" person.

In another example, while the user is wearing the wearable fitness monitor 102, the wearable fitness monitor 102 may calculate and store a user's step count while the user is wearing the wearable fitness monitor 102 and then subsequently transmit data representative of step count to the user's account on a web service like www.fitbit.com, to a mobile phone paired with the portable biometric monitoring unit, and/or to a standalone computer where the data may be stored, processed, and visualized by the user. Indeed, the device may measure, calculate, or use a plurality of other physiological metrics in addition to, or in place of, the user's step count. These include, but are not limited to, caloric energy expenditure, floors climbed or descended, heart rate, heart rate variability, heart rate recovery, location and/or heading (e.g., through GPS technology including a GPS receiver), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, and respiration rate. Some of this data may be provided to the wearable fitness monitor from an external source, e.g., the user may input their height, weight, and stride in a user profile on a fitness-tracking website and such information may then be communicated to the biometric tracking device and used to evaluate, in tandem with data measured by the biometric sensors 110, the distance traveled or calories burned of the user. The device may also measure or calculate metrics related to the environment around the user such as barometric pressure, weather conditions, light exposure, noise exposure, and magnetic field.

As mentioned previously, collected data from the wearable fitness monitor may be communicated to external devices through the communications interface. The communications interface may include wireless communication functionality so that when the wearable fitness monitor comes within range of a wireless base station or access point, the stored data automatically uploads to an Internet-viewable source such as a website, e.g., www.fitbit.com. The wireless communications functionality may be provided using one or more communications technologies known in the art, e.g., Bluetooth, RFID, Near-Field Communications (NFC), Zigbee, Ant, optical data transmission, etc. Some of these communications technologies such as Bluetooth and NFC may be characterized as low power and/or short range in comparison to some other wireless communications technologies such as cellular and Wifi. In some embodiments, the wearable fitness monitor also contains wired communication capability, e.g., USB.

Other implementations regarding the use of short range wireless communication are described in U.S. patent application Ser. No. 13/785,904, titled "Near Field Communication System, and Method of Operating Same" filed Mar. 5, 2013 which is hereby incorporated herein by reference in its entirety.

It is to be understood that FIG. 1 illustrates a generalized implementation of a wearable fitness monitor 102 that may be used to implement a portable wearable fitness monitor or other device in which the various operations described herein may be executed. It is to be understood that in some implementations, the functionality represented in FIG. 1 may be provided in a distributed manner between, for example, an external sensor device and communication device, e.g., a chest-strap heart rate sensor that may communicate with a wearable fitness monitor.

Moreover, it is to be understood that in addition to storing program code for execution by the processing unit to affect the various methods and techniques of the implementations described herein, the memory 108 may also store configuration data or other information used during the execution of various programs or instruction sets or used to configure the wearable fitness monitor. It is to be further understood that the processing unit may be implemented by a general or special purpose processor (or set of processing cores) and thus may execute sequences of programmed instructions to effectuate the various operations associated with sensor device syncing, as well as interaction with a user, system operator or other system components. In some implementations, the processing unit may be an application-specific integrated circuit (ASIC) or programmable hardware, such as a FPGA.

Though not shown, numerous other functional blocks may be provided as part of the wearable fitness monitor 102 according to other functions it may be required to perform, e.g., environmental sensing functionality, etc. Other functional blocks may provide wireless telephony operations with respect to a smartphone and/or wireless network access to a mobile computing device, e.g., a smartphone, tablet computer, laptop computer, etc. The functional blocks of the wearable fitness monitor 102 are depicted as being coupled by the communication path 114 which may include any number of shared or dedicated buses or signaling links. More generally, however, the functional blocks shown may be interconnected using a variety of different architectures and may be implemented using a variety of different underlying technologies and architectures. With regard to the memory architecture, for example, multiple different classes of storage may be provided within the memory 108 to store different classes of data. For example, the memory 108 may include non-volatile storage media such as fixed or removable magnetic, optical, or semiconductor-based media to store executable code and related data and/or volatile storage media such as static or dynamic RAM to store more transient information and other variable data.

The various methods and techniques disclosed herein may be implemented through execution of one or more sequences of instructions, e.g., software programs, by the processing unit 106 (e.g., a generalized or specialized processor) or by a custom-built hardware ASIC (application-specific integrated circuit) or a programmable hardware device such as an FPGA (field-programmable gate array), or any combination thereof within or external to the processing unit 106.

Further implementations and implementations of wearable fitness monitors can be found in U.S. patent application Ser. No. 13/156,304, titled "Portable Biometric Monitoring Devices and Methods of Operating Same" filed Jun. 8, 2011, which is hereby incorporated herein by reference in its entirety.

In some implementations, the wearable fitness monitor may include computer-executable instructions for controlling one or more processors of the wearable fitness monitor to obtain biometric data from one or more biometric sensors. The instructions may also control the one or more processors to receive a request, e.g., an input from a button or touch interface on the wearable fitness monitor, a particular pattern of biometric sensor data (e.g., a double-tap reading), etc., to display an aspect of the obtained biometric data on a display of the wearable fitness monitor. The aspect may be a numerical quantity, a graphic, or simply an indicator (a goal progress indicator, for example). In some implementations, the display may be an illuminable display so as to be visible when displaying data but otherwise invisible to a casual observer. The instructions may also cause the one or more processors to cause the display to turn on from an off state in order to display the aspect of the biometric data.

Motion Sensors

Motion sensors provide an output a signal responsive to motion experienced. Examples of motion sensors include accelerometers, gyroscopes, compasses, switches (for example, mechanical), GPS modules, piezoelectric film and/or pedometers to determine, calculate and/or detect one or more steps of the user; notably, the exemplary motion sensor may be incorporated into portable monitoring devices such as wearable fitness monitors.

The portable monitoring device may estimate, calculate and/or determine, calorie consumption, burn and/or expenditure using data which is representative of the intensity of user motion—for example, as provided or determined by one or more single axis or multi-axis accelerometers. In one embodiment, the signals from the one or more accelerometers may be filtered using time domain or frequency domain filtering techniques to produce a parameter indicative of the intensity of user motion, often referred to as a "count". A count may be computed as the sum of the rectified filtered accelerometer output taken over a suitable time epoch, for example, 10 seconds, with or without additional processing such as thresholding and/or saturation. The portable monitoring device may calculate, determine and/or estimate calorie consumption, burn and/or expenditure as a function of the current count value or a sequence of count values. Further descriptions of various motion sensors are provided in U.S. Patent Application Publication No. 2015/0134268, titled PORTABLE MONITORING DEVICES AND METHODS OF OPERATING SAME, filed on Jan. 22, 2015, which is incorporated by reference in its entirety.

An accelerometer is often used as a motion sensor. For clarity and ease of discussion, this disclosure adopts a coordinate system as outlined in FIG. 2. It is to be understood that coordinate systems, as a rule, are a matter of convenience and may be arbitrarily defined—for example, a tri-axial accelerometer may be flipped upside down to reverse the orientations of two of the three axes of the tri-axial accelerometer or may be subjected to two 90° rotations about mutually-perpendicular axes to cause all three axes to be aligned differently from the conventions used herein.

Figure 2:
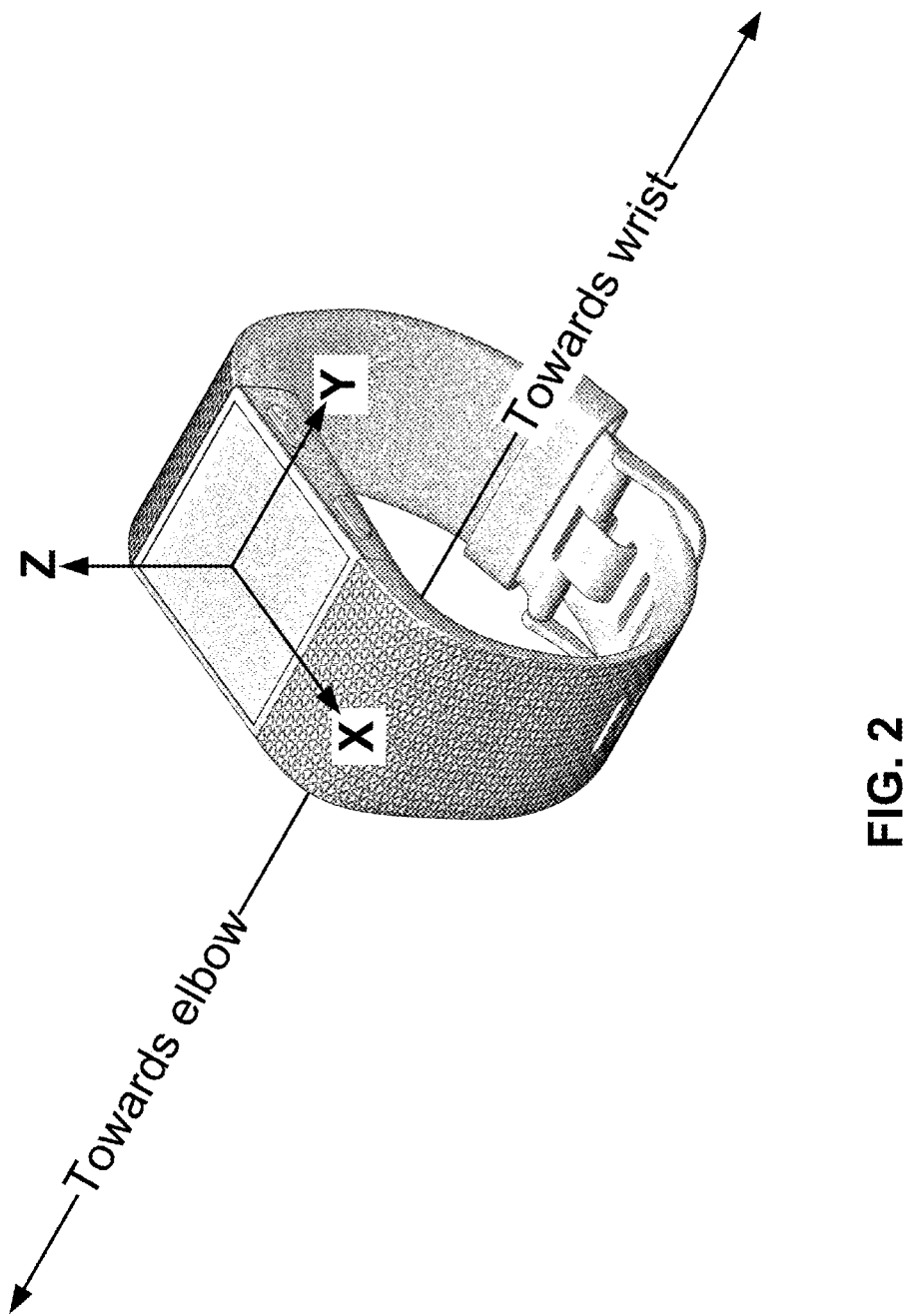
FIG. 2 shows one implementation of a wearable fitness monitor having an accelerometer, illustrating a coordinate system of the accelerometer.

To that end, it is to be understood that the techniques discussed herein may be practiced using tri-axial accelerometers (and their corresponding measurement outputs) that are aligned with coordinate systems different from the convention used in this disclosure (as outlined in FIG. 2). It is to be further understood that the data from tri-axial accelerometers that are aligned with other coordinate systems may still be used to perform the techniques discussed herein if the data from such tri-axial accelerometers is transformed in order to align with the coordinate system convention adopted herein or if the techniques outlined herein are adapted, e.g., transformed, to account for the shift in coordinate systems (for example, if an axis is reversed from the convention used herein, a condition stating that an acceleration along that axis be less than −0.125 g may have an equivalent condition in the new coordinate system that the acceleration along that axis be more than 0.125 g). Further descriptions of accelerometers are provided in U.S. Provisional Patent Application No. 62/054,345, titled WRIST-WEARABLE DEVICE WITH WATCH-CHECK GESTURE ACTIVATION, filed on Sep. 23, 2014, which is incorporated by reference in its entirety.

It is also to be understood that the accelerations obtained from the accelerometer(s) may be first subjected to one or more pre-processing steps prior to being used in the present techniques. For example, the accelerations may be used in raw form (counts or accelerations converted from counts, for example) or may first be smoothed or otherwise processed (e.g., by using a moving average filter) to reduce noise and produce a more stable signal.

As discussed above, the techniques of concepts presented herein are intended to provide more reliable, more responsive recognition of motion signatures while simultaneously having a low impact on battery life. As a result, in some cases herein, various operations that are discussed may be performed slightly differently in actual practice. For example, as part of one technique, the magnitude of acceleration measured by a tri-axial accelerometer may be evaluated to see if it exceeds a threshold acceleration.

Another type of motion sensor is an angular motion measurement system. A detailed description of angular motion measurement systems is provided in U.S. Provisional Patent Application No. 62/054,341, titled HIGH-DYNAMIC RANGE ANGULAR MOTION SENSING SYSTEM, filed on Sep. 23, 2014, which is incorporated by reference in its entirety. Such systems may obtain angular motion measurement data using a hybrid system incorporating two different, non-gyroscopic angular motion measurement sensors. Such a system includes, at a minimum, a multi-accelerometer angular rate sensor (MAARS), an accelerometer/magnetometer angular rate sensor (AMARS), and logic for determining which of the two angular rate sensors (ARS's) were to actively used to collect data at any given instant in time.

Applications of Wearable Fitness Monitors Requiring User Identification

Control Secure Devices and Other Appliances or "Things"

In certain embodiments, wearable fitness monitors are used to control or facilitate control of electronic and/or digital devices and systems such as household appliances, automobiles, door locks, and the like. Such devices may be secure in the sense that they cannot be controlled or otherwise accessed without a form of authentication (e.g., a password) or other user identification. In various implementations, the fitness monitor serves to identify a user and allow access a secure electronic device or system. This form of identification may have other applications such as enabling access to secure physical areas or property, and customizing user experiences/interfaces for a service. Further examples include controlling a television, unlocking and/or opening the door of a residence, office, car, or other locked space, providing a digital ID and password (pin or otherwise) to access a computer, banking account, online shopping site, or other computer account, changing the music played in a room for a specific user, selecting the goods to display to a user on a shopping site, etc.

Rewards and Incentives for Meeting Activity Thresholds

Similarly, wearable fitness monitors may be used to authenticate or otherwise identify a user when monitoring the user's behavior toward a reduction of insurance premiums or related incentive rewards programs. For example, a user who on average walks more than 10,000 steps per day for a duration of 6 months may receive a cash reward. A user who performs medium intensity exercise for 10 minutes (or more) for 150 minutes (or more) a week for 1 month may pay a discounted medical insurance premium. A user who performs vigorous intensity exercise for 10 minutes (or more) for 75 minutes (or more) a week for 1 month may receive discount coupons or cash cards at a selected retailer. A user who performs on average more than N exercises per week of a minimum duration T every 4 months may receive a cash reward (e.g., N=5, T=5 min). A user who increases daily activity by 10% over a baseline daily activity value for 6 months may obtain a reduced insurance premium for the following 6 months. In each of these and other cases, the wearer of the fitness monitor must be identified as the user before such rewards are distributed to the user. This identification can occur at different points in time as the user is wearing the device and making progress towards the goal. The points in time may be selected according to a set frequency, period, schedule (with different intervals between identification points to appear random) or triggered based on a condition that considers progress toward a goal (e.g., if the wearable fitness monitor detects activity of a given step rate, time period of activity, or an activity being performed).

Fitness Competition

The data from wearable fitness monitor may also be used to compete against friends (e.g., in a social network), coworkers, or in a game. For example, a user who runs a specific path the fastest may be granted a title (e.g., "king of the hill"). A user who has the most steps in a week (or any other time period) may be placed at the top of a leaderboard. A user in a digital race game may be ranked against peers on the basis of running distance in a month. In each of these and other cases, the wearer of the fitness monitor must be identified as the user before the fitness monitor's measured metric is ascribed to the competing user.

In some cases the competition may be individually based where the metrics of an individual are ranked or compared against other individuals. In other cases, the competitions may be group based, where groups are formed from multiple individuals and the metrics of the members of the group are aggregated (e.g., summed, averaged, etc.) and the aggregated metric of a group is compared against the aggregated metric of the other groups. Embodiments may allow groups to be formed based on an attribute such as a department, company, geography (state, city), a school, a dorm, a social group, a family connection, friend connection, favorite team, or any other suitable attribute. In other cases, embodiments may allow groups to be formed based on an invitation scheme.

Shared Devices

In some cases a wearable fitness monitor may be shared amongst multiple users. For example, a gym, household, school, work place, or any other community may provide a wearable fitness monitor to members of that community. The use of the wearable fitness monitor may be time-sliced among the member. Rather than requiring each user initiating a session with the wearable fitness monitor, the classification logic may authenticate the wearer of the classification logic and, once authenticate, correlate tracked activity data from the wearer's use of the wearable fitness monitor with the digital account of the wearer.

Motion Signatures and Features

In certain embodiments, the wearer of a fitness monitor is identified as the user by obtaining one or more motion signatures from the fitness monitor and determining whether such signature(s) are produced by the user's movement. Individual humans have movement characteristics which individually or collectively be used as a biometric identifier for the user. Such motion signatures are described further herein. These signatures and their comparison to reference features linked to the user may allow the wearable fitness monitor to authenticate or otherwise identify the wearer of the wearable fitness monitor. A motion signature may be obtained from a motion sensor such as one of the sensor types mentioned above. It may be viewed as a form of biometric information that can be collected or presented at any time to authenticate or otherwise identify the wearer of the wearable fitness monitor. The wearer of a fitness monitor is identified as the user when the motion signature (or the motion signature in combination with other wearer information) matches, to a degree required by an appropriate user classification procedure, the information in one or more reference features.

Examples of Motion Signatures

Many types of motion signatures may be obtained via data from motion sensors and may be used by the user identification logic. Some motion signatures may represent motion in the time domain (e.g., amplitude, power, intensity, phase, field strength, etc., each as a function of time). Others represent motion in the frequency domain (e.g., amplitude, power, intensity, phase, field strength, etc., each as a function of frequency). Other types of motion signatures are provided only in association with certain activity types such as running, walking, swimming, bicycling, rowing, weightlifting, etc. For example, curl repetition count is a motion signature that is associated with weightlifting but not running or bicycling.

Some other types of motion signature employ a single cycle which may be characterized by its "profile," which may have either time or frequency as an independent variable. In use, the cycle motion signature is compared against a reference cycle feature, with the comparison matching features of the cycle such as total magnitude and/or duration (e.g., peak-to-peak), maximum or minimum magnitude, maximum positive or negative slope, the number and relative locations of inflection points, envelope, etc. The comparison can be performed by many different techniques including pattern recognition algorithms or classification algorithms known to those of skill in the art.

Other examples of motion signatures include step count, step rate, cadence, a metric derived from an amplitude of a periodic motion, a biking cadence, a rowing rate, a resistance-based repetition rate, a typing speed, a zero crossing rate, a peak-to-peak time, an arm swing rate, or a combination thereof.

As explained, motion signatures are obtained from data taken from motion sensors. The data may be processed little or substantially to obtain motion signatures. Further, the motion sensor data used to obtain the motion signatures may be the raw "absolute" signal, or may be obtained after filtering (by, e.g., bandpass filtering, low pass filtering), scaling, and the like. In some examples, the 2-norm of the 3-axis accelerometer motion signal may be used in lieu of or in combination with the (x, y, z) signal features to provide information used in a motion signature.

Motion signatures representing repetitive movement (not just a cycle) may be obtained using, e.g., data processed to obtain peak counts, zero crossings, spectral information from, e.g., a FFT, and the like. A Fourier series decomposition may be performed to extract the contributions of multiple periodic motions to sensor signal. These contributions may be harmonics associated with, e.g., steps and arm motion. Each harmonic may be a motion signature and/or the ratio of the harmonics' powers may be a motion signature. For example, it has been found that a user's step impact has a big effect on the power observed in higher harmonics. It is to be appreciated that although some embodiments have been described in the context of harmonics, other embodiments can operate on any contribution of a spectral component.

It should be understood that the wearing configuration of a fitness monitor affects the resulting motion signature. For example, a single user motion may produce one motion signature when obtained using a fitness monitor clipped to the user's hip and a second motion signature, different from the first motion signature, when obtained using a fitness monitor worn on the user's wrist. The motion signature analysis may therefore account for the type and worn location of the fitness monitor.

Examples of Reference Motion Features

Figure 3:
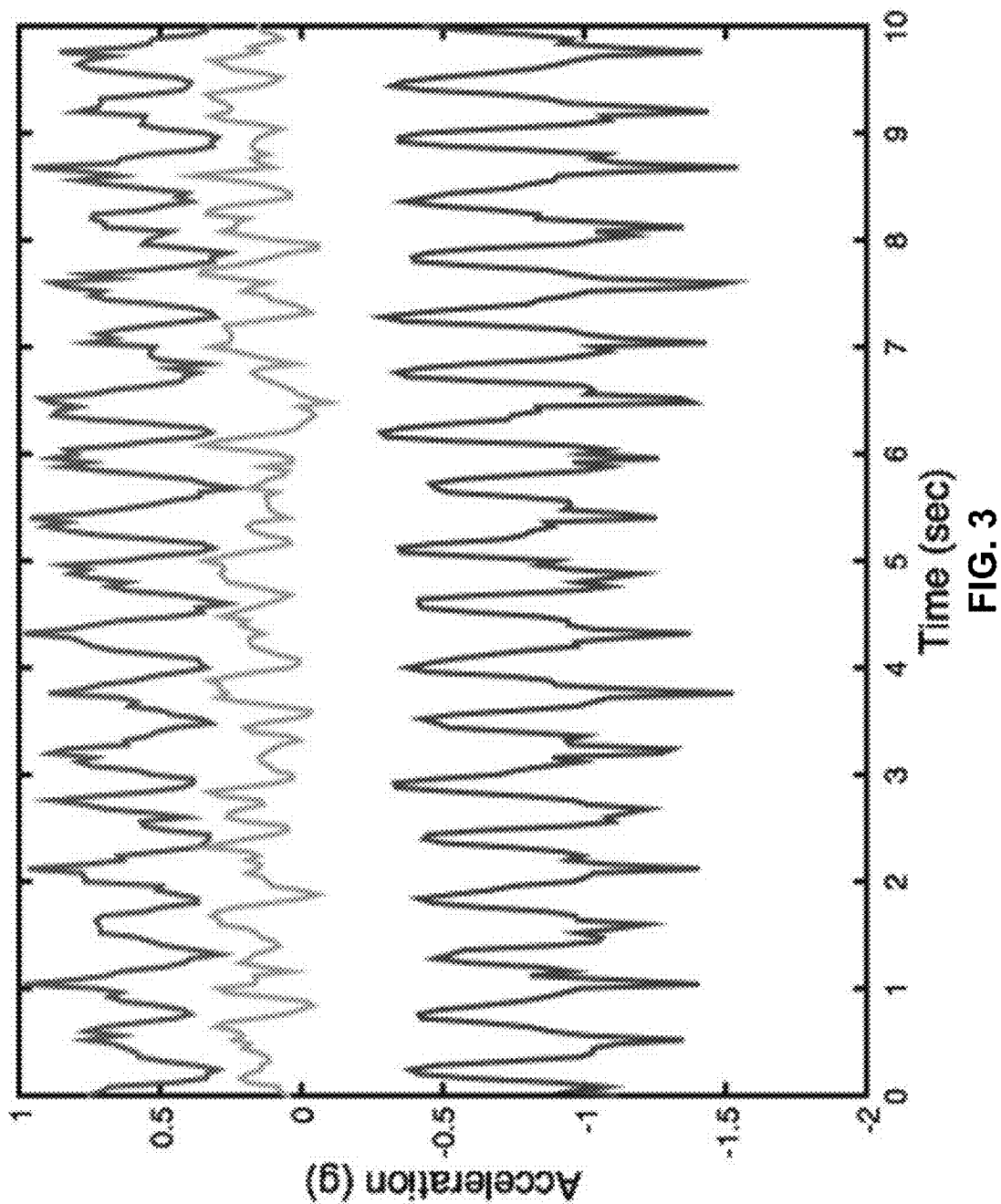
FIG. 3 shows a representative 3-axis accelerometer signal from a wearable fitness monitor worn on the wrist of a user who is walking.

As explained, a user may be recognized by comparing a user's reference motion feature(s) to a motion signature measured by a wearable fitness monitor. A few examples of reference motion features will now be provided. FIG. 3 shows a representative 3-axis accelerometer signal from a wearable fitness monitor worn on the wrist of a user who is walking. Using an accelerometer, motion signatures such as the step rate (e.g., steps/min) and signal energy may typify a user. For example, for a user who is walking, the accelerometer signal energy increases with step rate. A user may be identified, distinguished from another user, or determined to be a fake by comparing the pair of motion signatures (step/min, signal energy) from the motion signal provided by the wearable fitness monitor to data characterizing the user's walk (e.g., features from signals previously supplied by the user or an entity responsible for enrolling the user and characterizing the user's walk). In various embodiments, trusted information characterizing movement typical of the user is referred to as a reference motion feature for the user.

Figure 4:
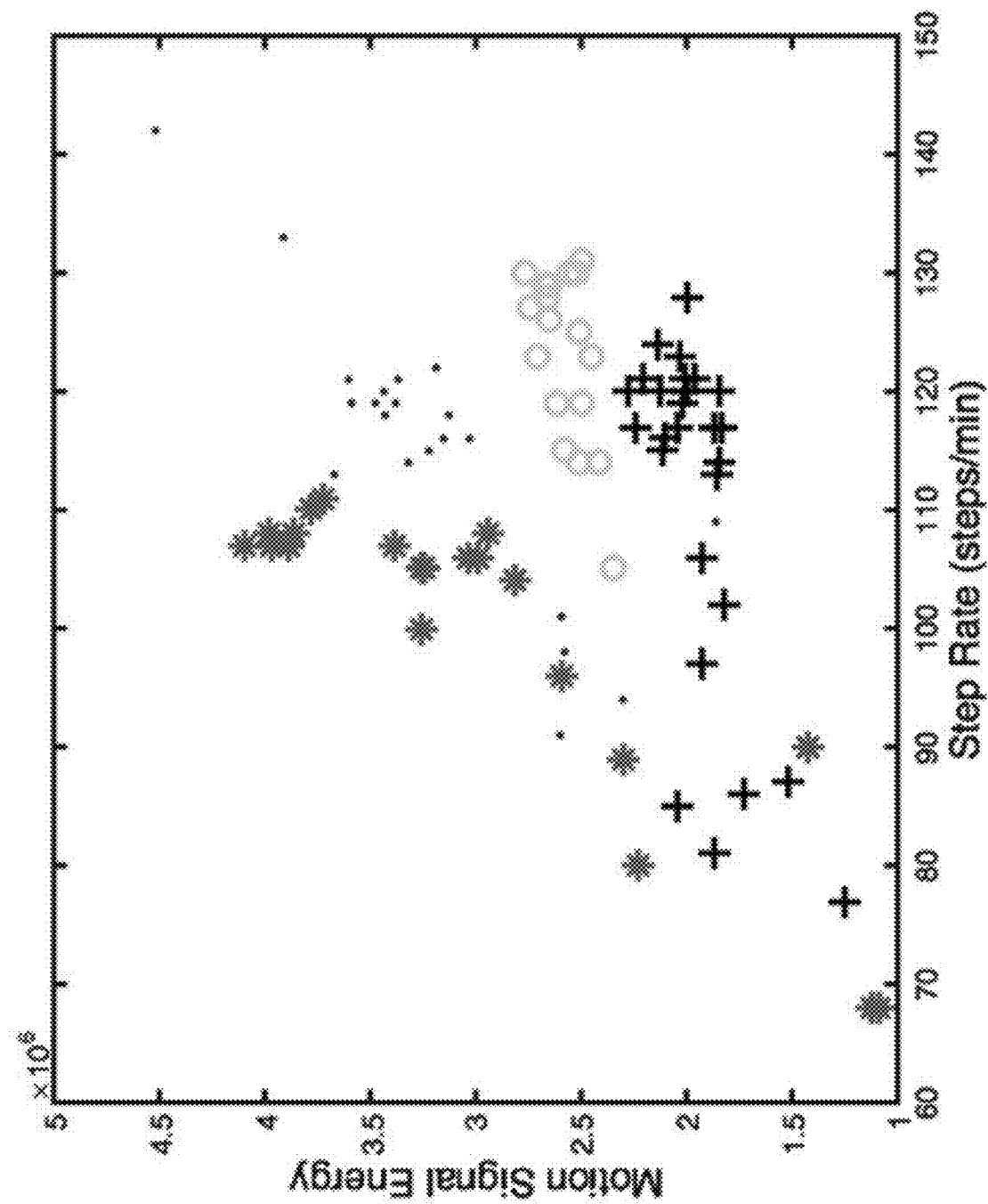
FIG. 4 depicts the step rate and signal energy for 4 unique users.

FIG. 4 depicts the step rate and signal energy for 4 unique users. The curve may be approximated as a line and a fitness monitor or the wearer of the fitness monitor may be classified by the nearest line to the data from the wearable fitness monitor (i.e., to one or more motion signatures). If the data does not lie within a reasonable limit to the line, the data may be considered fake (e.g., in the sense of a linear discriminant). A line is used in this example, but any model may be employed such as an arbitrary polynomial, lookup table, etc. Also, the classifier employed may be a neural network, support vector machine, random forest, decision tree, or other machine learning or heuristic algorithm.

Figure 5:
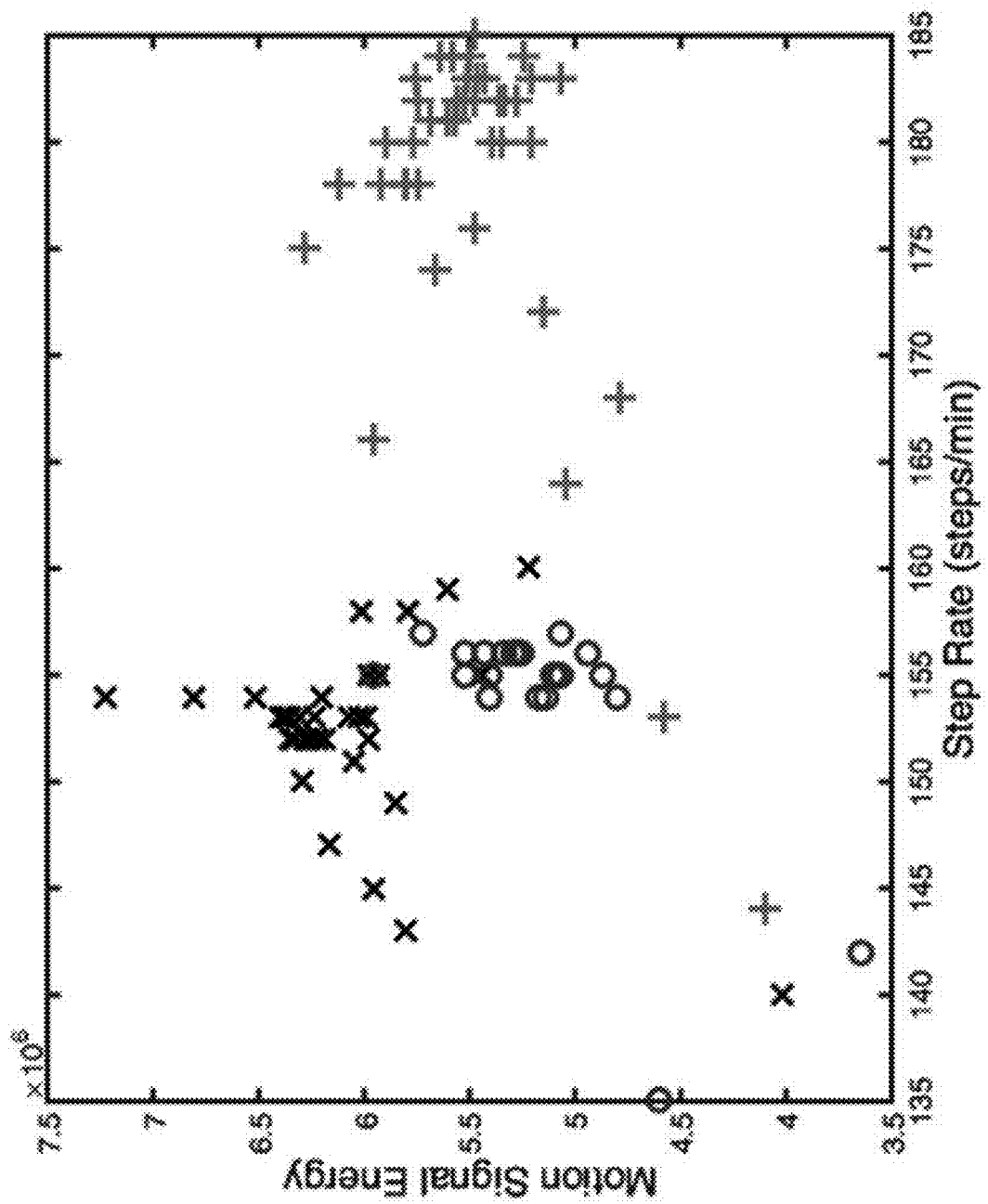
FIG. 5 depicts the step rate and signal energy for 3 unique users for a run.

Similarly, the step rate and signal energy during a run may identify the user, distinguish the user from another, or determined to be a fake. In embodiments where there is no enrollment for a user, default curves or lookup tables for these quantities may be employed. FIG. 5 depicts the step rate and signal energy for 3 unique users for a run.

Figure 6:
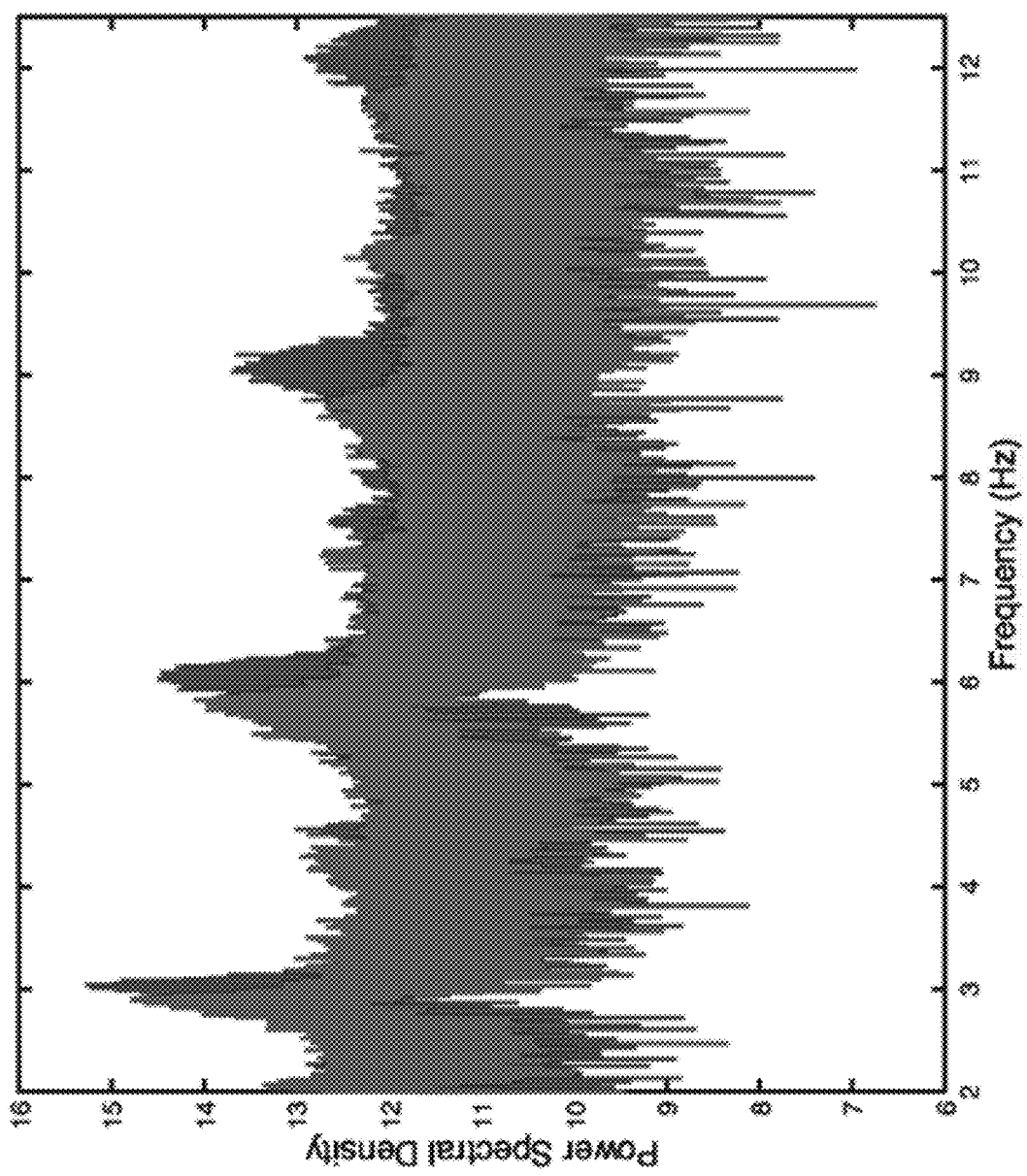
FIG. 6 depicts power spectral density of motion data of two unique users who are otherwise indistinguishable in running by step rate and signal energy.

In other embodiments, one user is distinguished from another by the spectral characteristics of the motion data. For example, where the spectral characteristic is a harmonic, the ratios of the second to first harmonic, third to first harmonic, and third to second harmonic observed in the 2-norm of a 3-axis accelerometer may be used. Higher harmonic content corresponds to more impact in walking. Similarly, the approach can be used for running. FIG. 6 depicts two unique users who are otherwise indistinguishable in running by step rate and signal energy, but are clearly distinguished by motion harmonics. Harmonic features may also be used in combination with the aforementioned walking/running features.

In other embodiments, the accelerometer motion signal is split into "cycles" (e.g., periods between two steps), aligned, time warped, and used to construct a composite or typical step profile for a user by which features such as the (x, y, z) axis peak-to-peak heights, envelopes, and peak-to-peak duration may be used to build a model of the user's typical motion. A "cycle-type" motion signature and associated reference motion feature may be used to identify a user in the manner described elsewhere herein. For example, a machine learning algorithm such as an LDA classifier, an artificial neural network, decision tree, support vector machine, or the like may be used to classify the user.

The aforementioned examples with an accelerometer are presented for illustrative purposes. In several other embodiments the wearable fitness monitor may have a gyroscope and similar or identical approaches may be employed in lieu of or in combination with an accelerometer. In all mention of signal data and signal processing operations performed, they may be performed on the raw "absolute" signal, or after filtering (e.g., bandpass filter, low pass filter), scaling, and the like.

The wearable fitness monitor may store one or more invalid motion features that each individually or collectively characterize motion likely to be faked (e.g., performed by a non-human). To detect fakes, the user's identity may be rejected based on an invalid motion feature that characterizes a detected step rate being too consistent (e.g., not varying by more than 5 steps/min from minute to minute over a 10 minute time window) or the motion being too periodic (e.g., each "cycle" of motion corresponding to a step being nearly identical to the previous), the signal energy being contained to nearly one axis of motion (e.g., through principal component analysis with over a threshold value (e.g., 50%) of the 2-norm of a 3-axis accelerometer signal being comprised of one motion axis), the duration of motion being too long (e.g., over 1 hour with no breaks), the motion observed on an accelerometer lacking high harmonic structure (e.g., being too smooth or sinusoidal, no clear presence of integer harmonics from the fundamental step frequency), or too erratic (e.g., 50% or more in peak-to-peak amplitude on an accelerometer over several "step" cycles). The wearable fitness monitor may store one or more invalid motion features that each individually or collectively characterize motion likely to be performed by a non-human.

Accordingly, a feature may thus be viewed broadly as data or logic that defines an expected signature of a user, either in the positive (e.g., reference motion signatures) or in the negative (e.g., invalid motion features). Such features may be expressed in a data driven manner (such as through a line, curve, graph, data point), functionally (e.g., logic that defines an expected threshold around a given motion signature), or some combination thereof. And illustrative example of a functional expression of a feature is an invalid feature that specifies that motion signatures that do not exceed a minimal variance are to result in deauthenticating the wearer, as may be the case where a mechanical device may be causing the motion data detected by the wearable fitness monitor. Thus, to execute this invalid feature, the classification logic may analyze the motion signature to determine whether the cycles represented by the motion signature vary beyond a threshold.

Location and Proximity Signatures and Features

In embodiments where the wearable fitness monitor comprises a location sensor (e.g., GPS, WiFi interface) or is in communication with a device that has a location sensor (e.g., a smartphone), location may be used to determine that the wearable is not with the intended user. For example, if the activity data provided by the wearable fitness monitor does not spend significant periods of time at the user's registered home and/or workplace (e.g., at least 8 hours at home), then the activity data may be classified as fake in relation to a cash incentive program or competitive challenge. In another embodiment, if the wearable fitness monitor is linked to the user's smartphone (e.g., via an account on an app running on the phone) but is not in proximity of the phone or does not "sync" data with the user's phone for a period of time (e.g., 1 week), then the activity data provided by the wearable fitness monitor may be rejected as fake for the purposes of a cash incentive program or competitive challenge.

In another embodiment, the wearable fitness monitor comprises a wireless communication system such as Bluetooth, Bluetooth Low Energy, Near Field Communication, Wifi, Body Area Network (e.g., communication routed through the body), and the like. In a manner similar to using a location sensor (e.g., GPS), the device or a system incorporating the device (e.g., a mobile phone and the wearable fitness monitor or a cloud-based server and the wearable fitness monitor) may reject data from the device as a fake or de-authenticate the user based on an inference of the user's location from communication over the wireless communication system. For example, the names of enrolled or commonly observed Wifi networks in the user's typical areas of movement (e.g., home, office, coffee shops, city/town) may be used to determine if the wearable fitness monitor is in a foreign environment, which may trigger a de-authentication. In such case, the device may prompt the user to re-authenticate by verifying a code provided by a trusted device (e.g., a mobile phone in which authentication is achieved via fingerprint or PIN code) or any of the authentication methods described in this disclosure. Prompting may occur by a vibration or haptic interaction from the wearable fitness monitor. Prompting may occur at the next moment in which the wearable fitness monitor's user interface is engaged (e.g., upon pressing a button or providing a motion gesture such as moving a wrist wearable toward the face). Notably, in the present embodiments, it is not necessary that the system infer the geographical location (e.g., address, latitude and longitude) of the user based on the communication data—it is sufficient to maintain a list of networks and/or devices that are in communication with the user.

In an embodiment, the wearable fitness monitor includes a Body Area Network communication system. When the user wears the wearable fitness monitor (e.g., on a wrist, clipped to a bra, on clothing), the device may transmit data through the user's body to another device that is in close proximity or in contact with the user. The user may touch a door knob that likewise includes a Body Area Network communication system and the door knob may unlock in response to the user's touch. Similarly, the user may touch or come in close proximity (e.g., less than 1 cm) to an automobile door handle, secured door in an office, etc., and the lock may disengage and/or open in response. The same touch and/or proximity may engage "syncing" of the wearable fitness monitor in the sense of transmitting activity, sleep, and other biometric data to the device that is in proximity and, thereafter, a cloud-based service (e.g., www-.fitbit.com). For example, a user may have a Body Area Network enabled lamp at home and touching the lamp may set the color and/or intensity of the light based on the user's preferences (including time of day) and also initiate the transmission of the wearable fitness monitor's activity data to the lamp (if so enabled to receive this data) or other communication hub (e.g., a computer in the user's residence).

Heartbeat Waveform Signatures and Features

In one embodiment, a user may authenticate to a wearable fitness monitor through features of a heart rate sensor, such as an electrocardiogram (ECG).

In an embodiment where the wearable is a bracelet, the device may contain a two electrode system where one electrode (lead 1) is in contact with the wrist and an electrode on the outer surface of the bracelet (lead 2) that is accessible by the opposite hand. When the opposite arm/hand makes contact with the bracelet (lead 2), a conductive path across the user's torso is created and an ECG signal can be collected for multiple heart beat cycles or for some duration of time (for example 10 heart beats or 10 seconds).

The ECG waveform collected is then post-processed into a signature waveform. This may involve techniques such as overlapping the periodic components of the waveform (e.g., individual PQRST sections), alignment, normalization, outlier removal, and linear/nonlinear filtering, outputting a composite or typical PQRST waveform signature.

Figure 7:
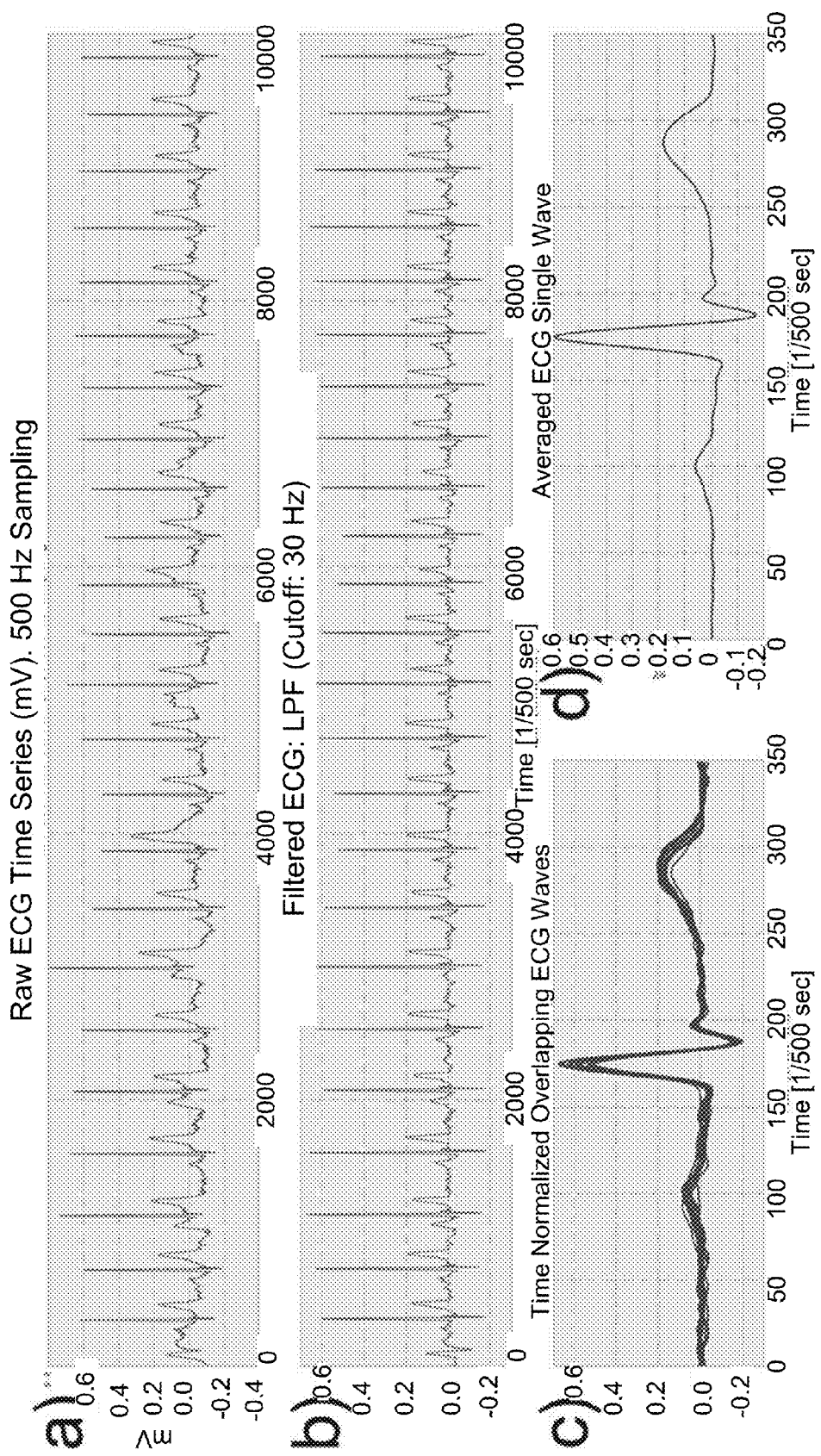
FIG. 7 shows examples of heart beat waveform data obtained from post-processing.

FIG. 7 shows examples of data obtained from post-processing. Panel (a) of FIG. 7 shows the raw ECG waveform acquired from the wearable fitness monitor. Panel (b) of FIG. 7 shows the ECG waveform after filtering. Panel (c) of FIG. 7 shows overlapping multiple repeating PQRST waveforms. Panel (d) of FIG. 7 shows the final ECG signature waveform used for feature extraction.

Figure 8:
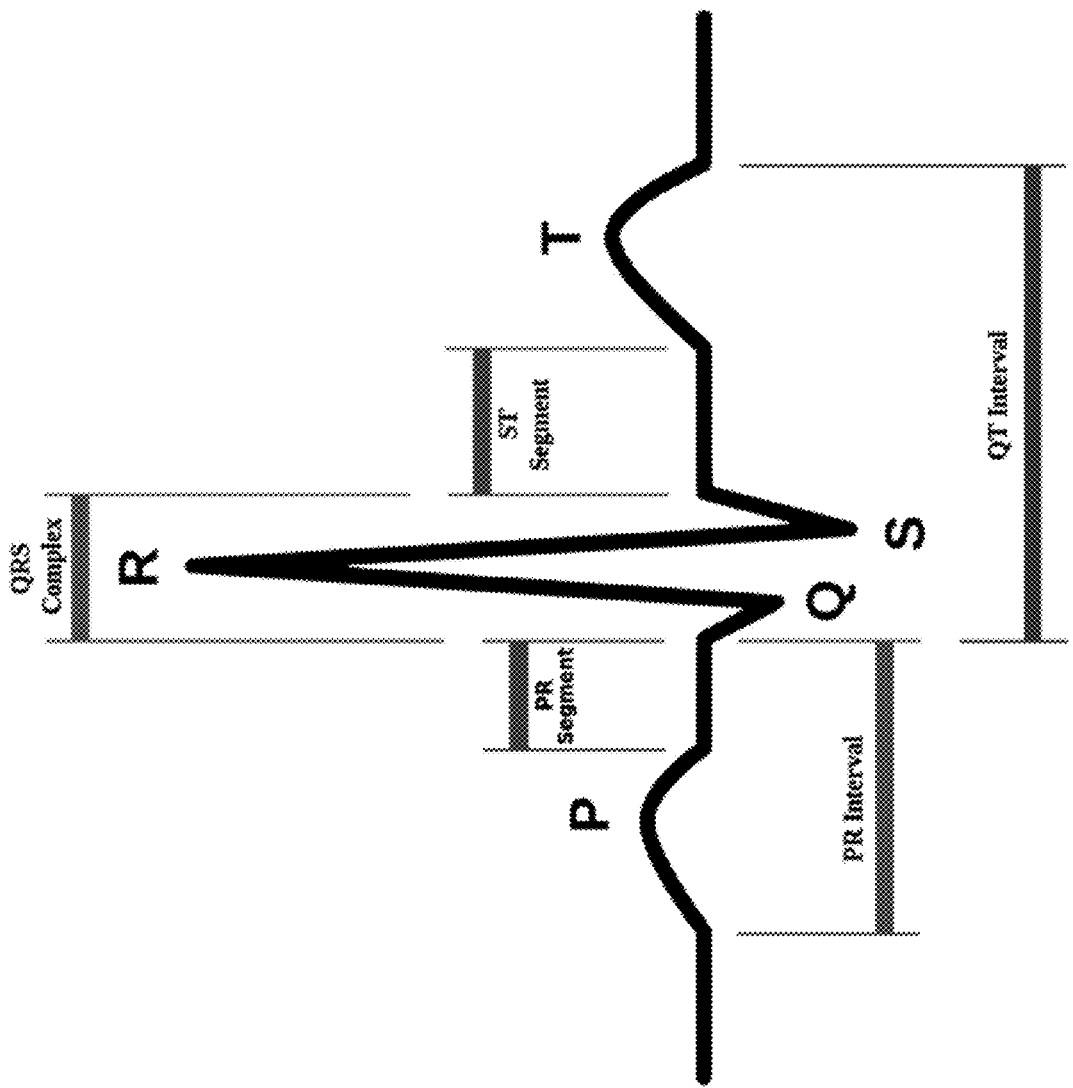
FIG. 8 shows a schematic illustration of a PQRST heart beat waveform.
Figure 9:
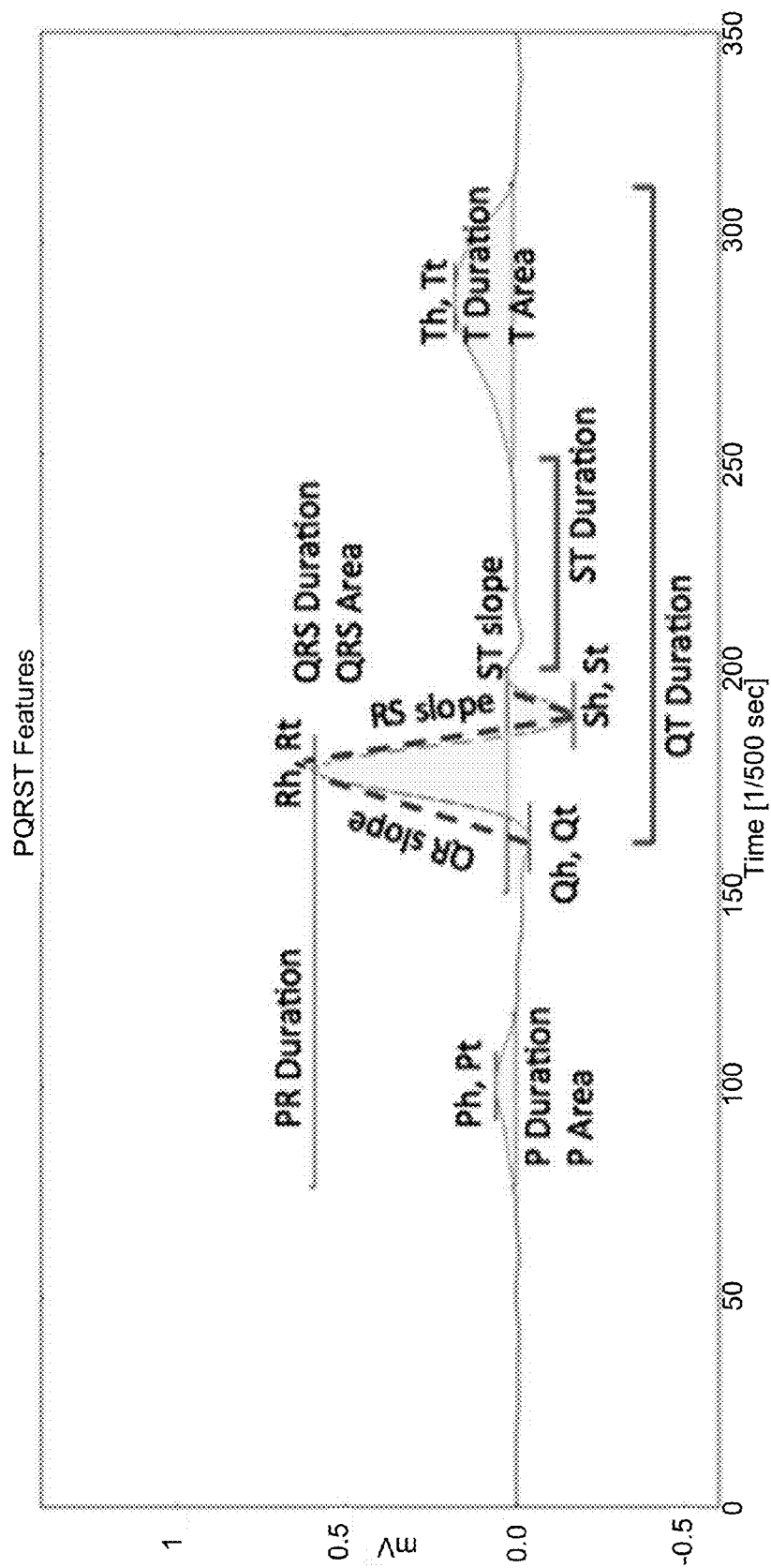
FIG. 9 illustrates a number of time domain features of a PQRST waveform.
Figure 10A:
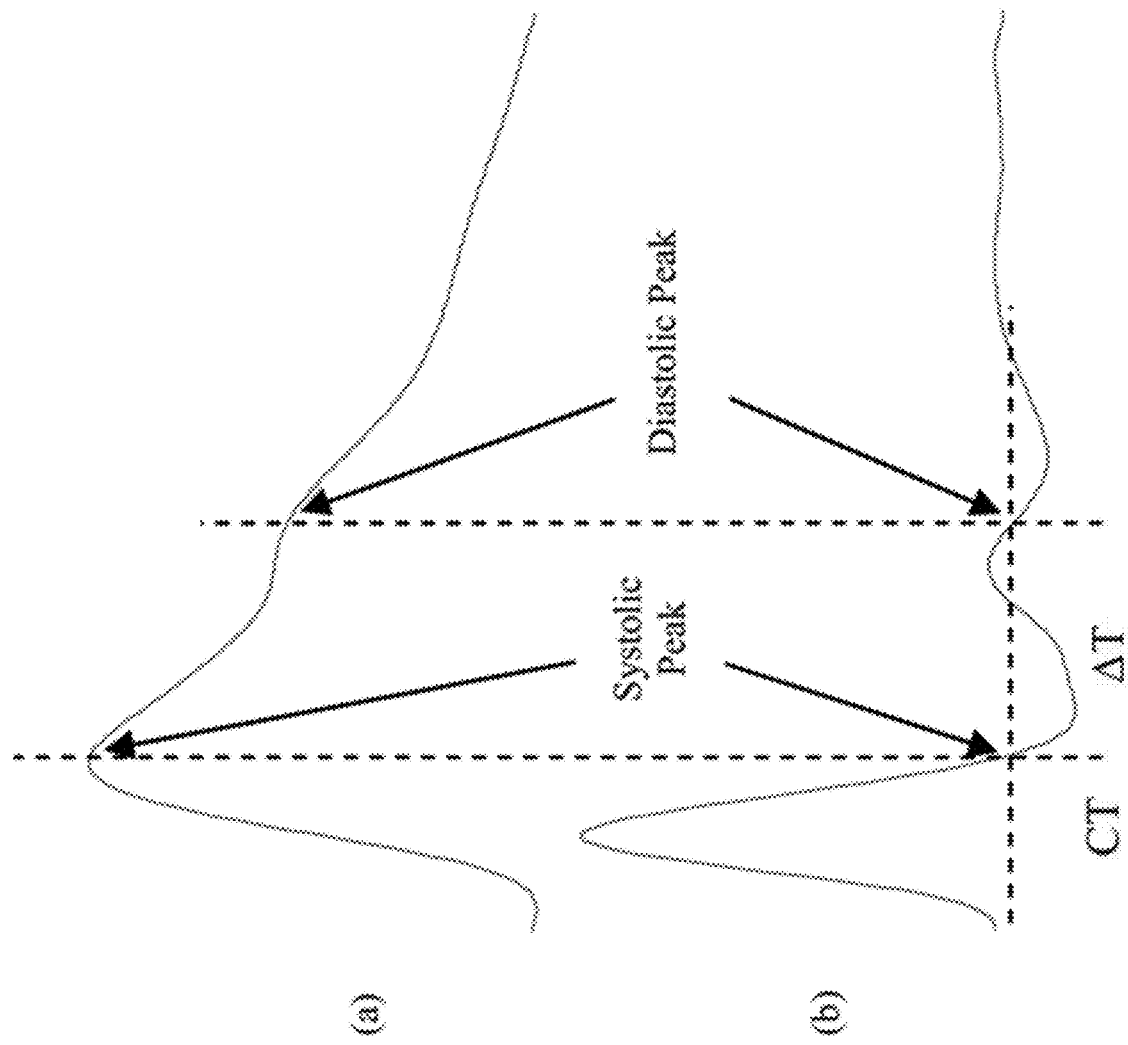
FIGS. 10A-10D depict representative features of the PPG waveform that may be used to identify the user.
Figure 10B:
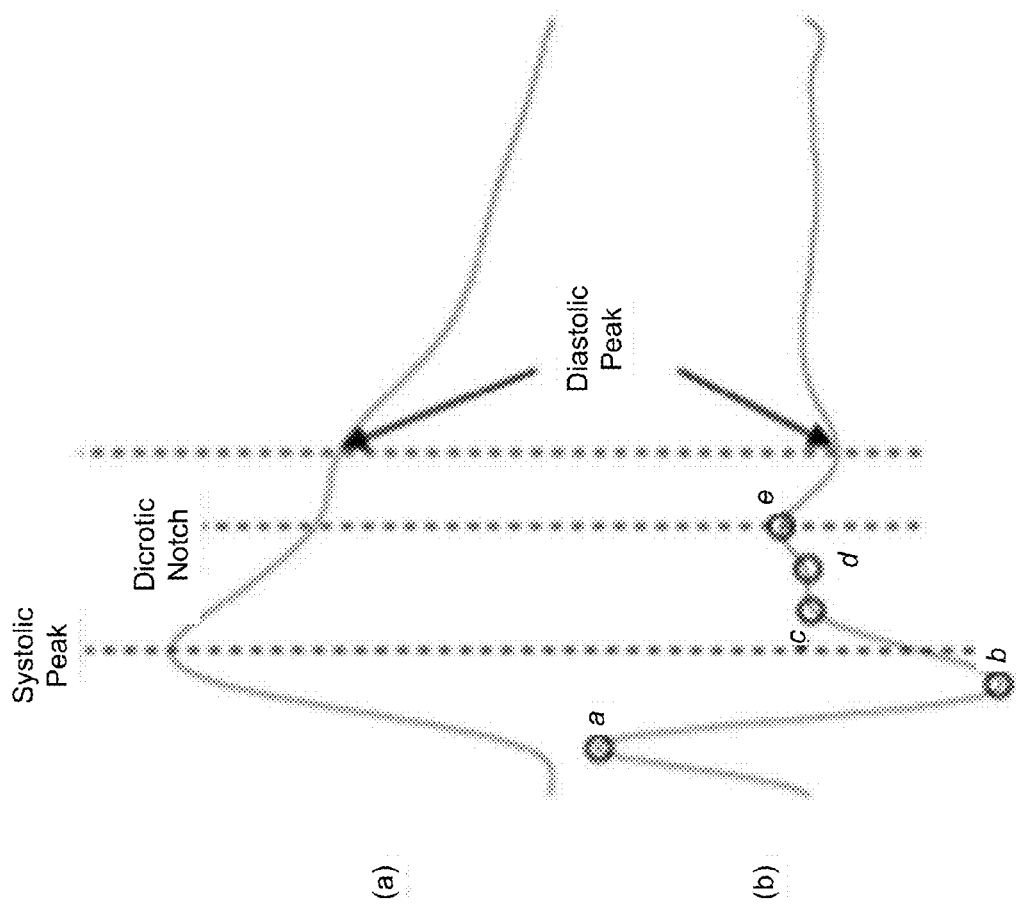
Figure 10C:
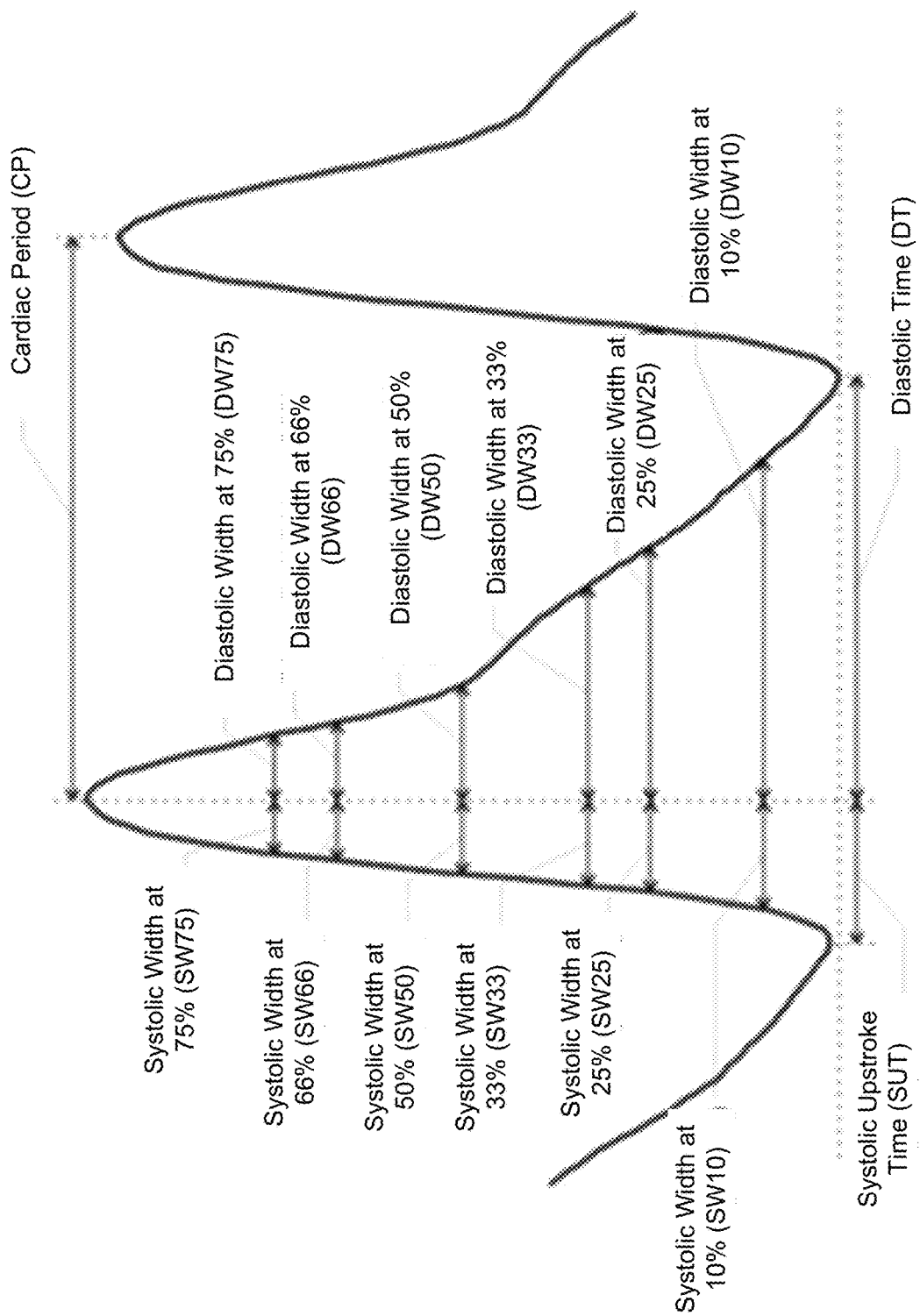
Figure 10D:
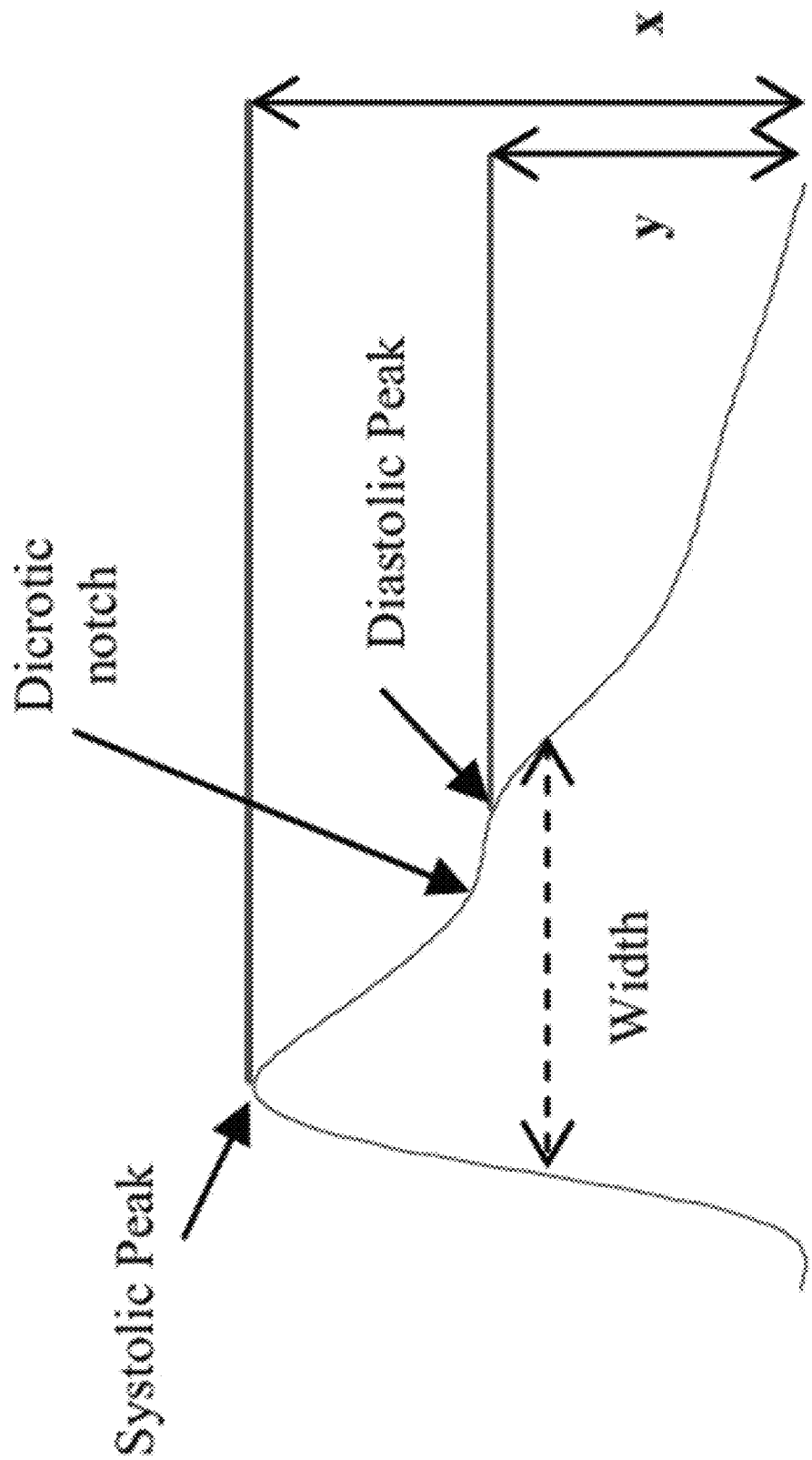

Signatures are then extracted from the final ECG signature waveform. These signatures may include pathological characteristics of the PQRST wave (shown in FIG. 8 below) use in cardiac monitoring such as the time and magnitude features of the PR interval, PR segment, QRS complex, ST segment, and QT interval. Signatures may also include other time domain (shown in FIG. 9 below) such as the slopes, areas, curvatures, and polynomial fits that may not directly have any direct physical or medical significance, but present uniqueness useful for authentication. Frequency domain characteristics can also be used as features such as Fourier and cosine transforms of the PQRST.

Authentication is determined through comparing the features of a reference ECG vs. that of a the ECG signal detected from the current wearer. Techniques for authentications could involve a combination of techniques such as neural network, support vector machine, logistic regression, naive Bayes, random forest, decision tree, or other machine learning or heuristic algorithms. After authentication is successful, the wearer can remain authenticated until the bracelet is determined to be off wrist, such as due to device removal or loss of contact.

In an embodiment where the wearable is a shirt, the device may provide continuous ECG measurements of the user. Similar to the embodiments described above, the ECG may be split into "beats", aligned, and used to construct a composite PQRST waveform over a moving window, which is then used to extract features to compare against a template for the user. In this embodiment, authentication may be continuous and the user may have a trust score that degrades if the features do not match for a period of time longer than the moving window. If the trust score goes below a designated threshold for a designated period of time, the user may be de-authenticated from the device. Additional features in this embodiment are that the presence of a live user may be determined both by a continuous (or nearly continuous) heart rate signal and that the user is wearing the shirt continuously. Using clothing to house a wearable fitness monitor is described in US Patent Application Publication No. 2010/0292599, which is incorporated herein by reference in its entirety.

In another embodiment, the wearable fitness monitor may include another type of heart rate sensor, such as a photoplethysmograph (PPG) sensor, for instance, to monitor the heart rate of the user when it is worn against the wrist. FIGS. 10A-10D below depict representative features of the PPG waveform (and its first derivative) that may be used to identify the user. The shape of the PPG waveform (e.g., in the sense of a template), which is correlated to the age of the user, may also be used as a feature after appropriate temporal and spatial normalization.

In addition, because a PPG is a light-based sensor and because many wavelengths of light are absorbed by skin pigmentation, a PPG sensor may be used to characterize the level of skin pigmentation for the wearer of the device based on a response of the PPG sensor. This may be used as an additional feature in a user authentication system. For example, if the intensity level of the PPG's light emitter is high but the return signal to the PPG's light detector is low, then the user has higher skin pigmentation. The ratio of the return signal to the emitter output may be used as a feature to characterize a user. Similarly, testing with different light intensities and/or wavelengths may provide a transfer function (or table lookup) for the user that may be used to identify the user. The wearable PPG sensor may have multiple wavelength LEDs that can be set to different intensities and/or multiple wavelength (e.g., spectral response) photodiodes to do this characterization.

In a related embodiment, the PPG sensor may be used to determine if the wearable fitness monitor is being worn. That is, if the PPG response is not representative of human skin (e.g., the return signal is low relative to the emitted output because there is nothing against the sensor), then the device can determine that it is not being worn, at least not on the wrist. This may be determined in combination with a motion sensor (e.g., that the device is stationary on a surface).

Similarly, the absence of a heart rate signal in the PPG data, or lack of heart rate variability (e.g., the duration between heart beats is too consistent), may be used to determine that activity data from the device is faked. Moderate to vigorous activity (e.g., walking or running) in the presence of low heart rate (e.g., below 60 bpm for walking and 90 bpm for running) in the PPG data may likewise indicate a fake.

In an embodiment, the wearable fitness monitor contains a motion sensor and an ECG. The user authenticates to the device with the ECG and the authentication may be lost if the motion signature is not representative of the registered user. In another embodiment, the wearable fitness monitor comprises a contact sensor (e.g., in the clasp, a PPG, or capacitive sensor against the wrist of the user) that detects when the sensor is removed from the user's wrist and then authentication is lost.

In an embodiment, the wearable fitness monitor contains a motion sensor and a PPG. Activity data from the device may be rejected as fake if the motion signature or the PPG-derived data do not correspond to the registered user or to human activity.

In an embodiment, the wearable fitness monitor contains an ECG and PPG. The user authenticates not only by matching the ECG morphological signatures and PPG morphological signatures with those previously enrolled by the user (e.g., the reference features), but also in comparing the heart rate and heart rate variability of the two signals to each other.

In another embodiment, the wearer of the device may be determined to not be the authorized user of the device based on the heart rate exertion of the user observed during an exercise. For example, the user may walk at a moderate pace and if the heart rate divided by the pace (as observed, say, by GPS) or step cadence is significantly higher or lower than is characteristic for the authorized user, the current user of the device is determined to not be the authorized user. In other embodiments where the wearable fitness monitor automatically tracks exercises such as elliptical, bicycling, and the like, equivalent metrics of heart rate per unit activity (e.g., elliptical strokes, bicycling pace) may be used to compare the current wearer of the device to the authorized user of the device.

Worn Detection

In some embodiments, optical monitors are used in the wearable monitor, implementing different modes of operation by emitting pulses of light and detecting light after it interacts with the user's skin or other tissue, to thereby capture data that may be used to obtain the user's heartbeat waveform, worn state, user characteristics, etc. In various embodiments, the optical monitor is used as a heartbeat waveform monitor, and while much of the following description refers to such monitors as heartbeat waveform monitors, such monitors need not be configured or designed to measure heartbeat waveforms. It is sufficient that the monitor emit and detect pulses and interpret the pulsing information to accomplish the described results.

In some embodiments, the current disclosure provides methods for operating a wearable fitness monitoring device having a heart rate monitor (HRM) in a low power state when the device determines that the device is not worn by a user, or is "off-wrist" when implemented in a wrist-worn device. This feature of the HRM is also referred to as an "automatic off" function. In some embodiments, the automatic off function is implemented by operating the HRM in an "unworn" (or "off-wrist") detection mode, and the automatic off function automatically turns off the heart rate monitoring operations of the HRM to conserve energy if the device determines that it is not being worn by the user. Other benefits of the automatic off function include providing more accurate heart rate estimation. For example, when an automatic off or automatic on (described below) is performed a heart rate detection algorithm may reset. In one implementation, the algorithm stops running when off-wrist is detected, and restarts when on-wrist is detected. When the heart rate monitor restarts, it resets.

In some embodiments, the current disclosure provides methods for operating a wearable fitness monitoring device having a heart rate monitor in a normal power state when the device is worn by the user, or "on-wrist" when implemented in a wrist-worn device. This feature of the HRM is also referred to as an "automatic on" function. In some embodiments, the automatic on function is implemented by operating the HRM in a "worn" (or "on-wrist") detection mode. The automatic on function automatically takes the HRM out of a low power state and turns on the heart rate monitoring operations of the HRM if the device detects motion and determines that it is worn by the user.

In some embodiments, the unworn (or off-wrist) and worn (or on-wrist) detection may be implemented by light (e.g., LED) probing, which emits light pulses and detects signals after the light pulses interact with the user's skin and tissues. In some embodiments, the unworn and worn probing may share some hardware, firmware, software, and/or parameters for light emission, light detection, and analyses of detected signals. In other embodiments, the two probing modes employ different hardware, firmware, software, and/or parameters for light emission, light detection, and analyses may be used for unworn and worn detection.

In some embodiments, the wearable fitness monitoring device goes in and out of the low power state regulated by a probe light (e.g., LED) and a motion detector, implementing automatic off and on functions. In the low power state, the heart rate monitor saves power by turning off, or scaling back operation of, its LED light source and its photodetector. In some embodiments, other light sources and light detectors (e.g., photodiodes, photomultiplier tubes, CCD, or CMOS) may be used to implement the automatic off and on functions.

Some embodiments provide a method of operating a heart rate monitor of a wearable fitness monitoring device having a plurality of sensors. The method includes: (a) operating the heart rate monitor in a first mode while also operating in a second mode configured to detect near proximity of the wearable fitness monitoring device to a user's skin, where the first mode is configured to determine one or more characteristics of a user's heartbeat waveform when the wearable fitness monitoring device is in near proximity to the user; (b) from information collected in the second mode, determining that the heart rate monitor is not proximate to the user's skin; and (c) in response to determining that the heart rate monitor is not proximate to the user's skin, ending operating the heart rate monitor in the first mode. In some embodiments, the one or more characteristics of the user's heartbeat waveform include the user's heart rate.

In some embodiments, the wearable fitness monitor includes a motion sensor, and the method further involving: prior to (c), determining from information output by the motion detecting sensor that the wearable fitness monitoring device has had been still for at least a defined period; and in response to detecting that the wearable fitness monitoring device has had been still for at least the defined period, performing (c). In some embodiments, prior to (a) while the first mode is not operating, the device (i) detects motion of the wearable fitness monitoring device using a motion detecting sensor and/or detecting proximity of the heart rate monitor to the user' skin by operating the heart rate monitor in a third mode; and (ii) initiates operation of the first mode of the heart rate monitor when the wearable fitness monitoring device is determined to be in near proximity to the user. Further implementations of operating heart rate monitors are provided in U.S. Pat. No. 8,948,832, titled WEARABLE HEART RATE MONITOR, filed on May 30, 2014, which is incorporated by reference in its entirety.

Other User Signatures and Features

In yet other embodiments, the wearable fitness monitor has a bioimpedance sensor (possibly sharing the same electrodes as the ECG) and the bioimpedance of the user is further used with the ECG and/or PPG to determine the current user of the wearable fitness monitor.

In yet another embodiment, the wearable fitness monitor has a fingerprint sensor (e.g., capacitive, ultrasound) that images the pattern of skin ridges on the finger(s) of a user to authenticate the user to a device (e.g., when the device is put on, when the device is used as a proxy for a credit card). The device may include an ECG, PPG, and/or bioimpedance sensor to further enhance the authentication system with user-specific biometric data. The device may maintain authentication through motion signatures of the user and PPG-based signatures of the user. Removal of the device (e.g., as detected by a capacitive sensor mounted on the back of a wrist wearable fitness monitor, as detected optically using an optical sensor (perhaps the same as a PPG sensor or an independent optical sensor), as detected by a sensor in the clasp of a wrist wearable fitness monitor) may de-authenticate the wearer of the device.

In another embodiment, the authorized user of the wearable fitness monitor may also have a smartphone that tracks user activity such as walking. If the smartphone walking activity does not match the time and approximate count of the wearable fitness monitor walking activity data for more than a threshold percentage (e.g., 50% of time over some period), then the data of the wearable fitness monitor is considered fake. If the wearable fitness monitor is used as a proxy for a credit card or other secure service, the authorization of the user is deactivated. Reauthentication may be established by displaying a code or image on the wearable fitness monitor and entering the same on the user's mobile phone. Likewise, if the mobile phone is used as a proxy for a credit card or other secure service, the authorization of it may be deactivated until reauthentication by matching a code or image to the wearable is performed. If the wearable fitness monitor comprises a location sensor (e.g., GPS), it may activate the sensor and broadcast its location when it next synchronizes to a cloud-based service.

In another embodiment, the wearable fitness monitor tracks the sleep of the user based on sensor data generated by the wearable fitness monitor. For example, the wearable may use motion data and/or heart rate data to infer when a user is asleep. Other examples include the use of skin temperature, galvanic skin response, SpO2, blood pressure, and time of day in combination with or in lieu of the preceding data to infer when the user is asleep. If the user is determined to be asleep by the wearable fitness monitor (or a system in communication with the wearable fitness monitor such as a mobile phone or cloud-based service), the authentication may be "blacked out" so that the wearable fitness monitor cannot be used to access secure digital accounts, open secure areas, etc. Upon waking, the user may retain authentication.

Skin Calibration

Skin color may be used to define one or more features of a user. In addition, skin color may affect heart rate measurements. This section discloses techniques for measuring skin color as a user feature and using skin measurements to improve measurements of other features such as heart rate.

Ambient light and skin color may make it difficult to extract a user's heart rate from a PPG signal. The effect of ambient light may be reduced by subtracting a value of the received detected light signal when the PPG light source is off from the value of the received detected light signal when the PPG light source is on (assuming that both signals are obtained in close temporal proximity to each other). The effect of skin color may be reduced by changing the intensity of the PPG light source, the wavelength of the light emitted from the light source, and/or by using the ratio or difference of received signal corresponding to two different wavelengths. Skin color may be determined by using user input (e.g. the user entering their skin color), an image of the person's face, etc., and may then subsequently be used to calibrate the algorithm, light source brightness, light source wavelength, and the receiver gain. The effect of skin color (and tightness with which the user is wearing the device) on the raw PPG signal may also be measured by sending in a signal of known amplitude to the light source(s) and then measuring the received signal from the photodetector(s). Such a signal may be sent for a prolonged period of time (so as to capture data through multiple expected heart beats) and then averaged to produce a steady-state data set that is not heart-rate dependent. This amplitude may then be compared to a set of values stored in a table to determine algorithm calibration, transmitter amplitude and the receiver gain.

In some embodiments, the disclosure provides methods and devices to accurately measure heartbeat waveform for different user characteristics, such as skin colors, motion, sweat, position, and physiologic state (e.g., skin thickness, body fat, etc.) of the users. Because darker skin has lower reflectance of light, the relations between photodetector reading and light pulse intensity, e.g., DAC, tends to have a lower slope than for paler skin. In some embodiments, the signals for skin characterization may operate intermittently at higher frequency than the light pulses of the first mode for heart rate monitoring.

Some embodiments provide a method for adjusting at least one setting for operating a heart rate monitor in a wearable fitness monitoring device. The method involves: (a) pulsing a light source in the heart monitor in a skin characterization mode by emitting a succession of light pulses, at least some having variable intensity with respect to one another; (b) detecting a variation in intensity of light from the light pulses emitted in the skin characterization mode after the light has interacted with the user's skin; (c) determining a response characteristic of the user's skin from the variation in intensity of light detected in (b); and (d) using the response characteristic of the user's skin to adjust a gain and/or light emission intensity of the heart rate monitor operating in a first mode for detecting one or more characteristics of the user's heartbeat waveform.

In some embodiments, the response characteristic is dependent on an opacity value of the user's skin. In some embodiments, operating in the first mode and operating in the skin characterization mode are performed concurrently. In some embodiments, operating in the first mode and operating in the skin characterization mode concurrently involves periodically determining a response characteristic of the user's skin while continuously operating in the first mode.

In some embodiments, operating in the first mode involves pulsing the light source in the heart rate monitor at a first frequency and detecting light from the light source, after the light has interacted with the user's skin, at the first frequency. Furthermore, operating in the skin characterization mode involves pulsing the light source in the heart rate monitor at a second frequency and detecting light from the light source at the second frequency.

In some embodiments, as described above, the wearable fitness monitor may store a reference feature relating to the response of a sensor to the skin of a user to later verify the user based on a current response of the sensor to the skin of the wearer of the wearable fitness monitor using, for example, the aforementioned techniques.

Comparing User Signatures to User Reference Features

Various classification and identification techniques may be applied to compare motion and/or other signatures to user reference features. Generally, such techniques determine whether or not it is likely that the motion signature obtained from a fitness monitor was created by a user in question wearing the device. In this way, a wearer of the fitness monitor can be authenticated or otherwise identified.

The logic used to compare a signature to a reference feature may be a classifier or other routine implemented on the fitness monitor and/or a secondary device as described elsewhere herein. As examples, the classifier employed may be an LDA classifier, neural network, support vector machine, random forest, decision tree, or other machine learning or heuristic algorithm.

As mentioned, the motion signal may be split into "cycles" (e.g., periods between two steps), aligned, time warped, and used to construct a composite or typical step profile for a user by which features such as the (x, y, z) axis peak-to-peak heights, envelopes, and peak-to-peak duration may be used to build a model of the user's typical motion. As with other types of signatures, this may be used by a machine learning algorithm such as a neural network, decision tree, support vector machine, and the like to classify the user.

In certain embodiments, the classification logic compares signatures to reference features and applies a level of confidence (provided directly or indirectly by the comparison algorithm) for authenticating or otherwise identifying the user. The confidence level for identifying the user may be set as appropriate for the application (insurance versus fitness credits in casual competition). The level may also be set for the type of classification algorithm used to compare the wearer's signature(s) to the user's reference feature.

Figure 11:
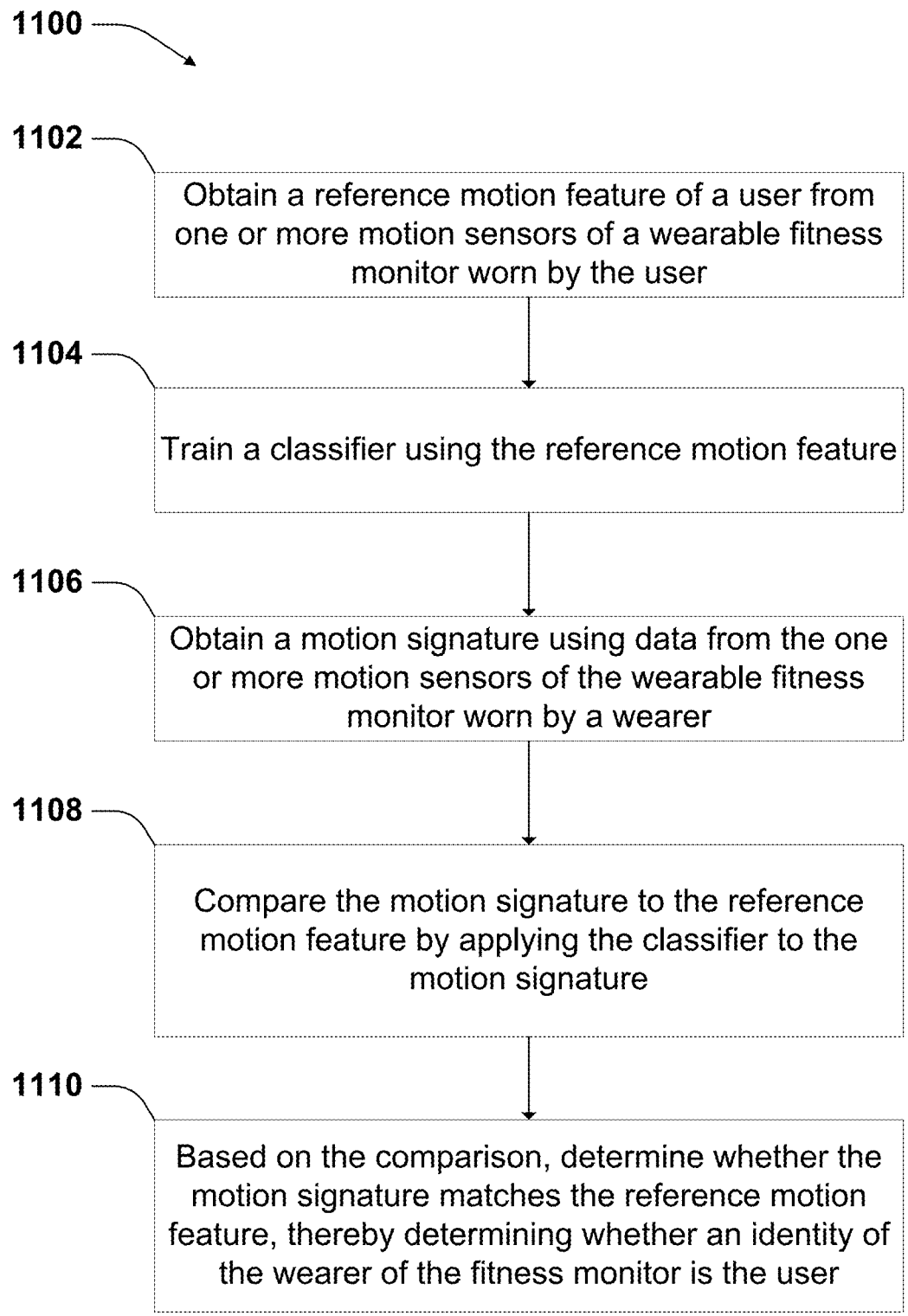
FIG. 11 shows a flowchart of a method for determining whether an identity of an instant wearer of a fitness monitor matches that of a user.

FIG. 11 shows a flowchart of a method for determining whether an identity of an instant wearer of a fitness monitor matches that of a user. If an instant wearer's identity matches that of the user, the instant wearer is authenticated as the user. For example, the user may be an owner or an authorized user of the wearable fitness monitor. Because the motion features of the user are provided as a reference against which a wearer's data are compared, the user is also referred to as the reference user herein.

In the implementations shown in FIG. 11, the operations of process 1100 are performed by a single wearable fitness monitor. In other implementations, some of the operations can be performed by the wearable fitness monitor, while others operations can be performed by an external device associated with the wearable fitness monitor such as smart phone, a personal computer, a tablet, or a webserver that is associated or communicatively linked to the wearable fitness monitor.

Process 1100 involves obtaining a reference motion feature of the reference user (or user as used elsewhere herein) using one or more motion sensors on the wearable fitness monitor worn by the user. See block 1102. The motion sensors may be selected from accelerometers, gyroscopes, GPS sensors, and other motion sensors described herein elsewhere. In some implementations, the reference motion feature comprises a motion cycle profile as described above and hereinafter at block 1206 of FIG. 12.

At block 1104, process 1100 involves training a classifier using the reference motion feature. In some implementations, the classifier is a binary classifier. In some examples, the classifier is a linear discriminant (LDA) classifier. Although an LDA classifier is provided as an example below, in various implementations, other classifiers described herein or known in the field may be used instead of or in combination with an LDA. For instance, clustering methods, neural networks, support vector machines, linear and nonlinear models, decision trees, etc., may be used as classifiers to classify the wearer. In some implementations, as described above for the LDA classifier, test data are classified as two classes. In some implementations, the classifier may determine three or more classes. In such implementations, the classifier may be implemented to authenticate three or more users. In some implementations, a C-class LDA classifier may be used, where C is not fewer than three.

A binary LDA provides a method to classify data in a multidimensional space into two classes: a target class and a non-target. Data points from each of the two classes are provided to train the classifier. The LDA projects the data points into a new space that best separates the two classes of the data points. More specifically, the projected data points have an optimal combination of mean difference and class variance, with the largest difference in means of the two classes and the smallest variance within each class. The LDA determines a hyperplane that separate the two classes of data. The projections of data points from the same class are very close to each other and at the same time the projected means of the two classes are as far apart from each other as possible. After the LDA classifier has been trained, the classifier is applied to a test vector. The test vector belongs to the target class if the test vector is located on the same side of the hyperplane as the target class, and the location of the hyper plane is defined by a threshold value.

The process 1100 further involves obtaining a motion signature from motion data of an instant wearer, using the one or more motion sensors of the wearable fitness monitor. See block 1106. The process 1100 shown in FIG. 11 uses the same motion sensors and the same wearable fitness monitor to obtain both the reference motion feature and the motion signature. However, in some implementations, the reference motion feature may be provided by sensors or wearable fitness monitors different from those producing the motion signature. For instance, the reference motion feature may be imported from another wearable fitness monitor or computer, and then stored on the instant wearable fitness monitor or an instant computer performing one or more operations of process 1100. Then the imported reference motion feature may be compared with the motion signature on the instant wearable fitness monitor or the instant computing device.

Operations 1102 and 1104 represent a different phase of the process from operations 1106-1110, with 1102 and 1104 performed initially and the result used repeatedly in 1106-10. Training the classifier is qualitatively different from using the classifier. Of course, 1102 and 1104 can be performed more than once to update the classifier as described in the example below. But typically a single trained classifier can be used repeatedly to determine identity.

In some implementations, the process involves obtaining two or more motion signatures from motion data of an instant wearer. In some implementations, the two or more motion signatures comprise two or more motion cycle profiles. In some implementations, the two more motion signatures comprise two different motion features, such as step rate and motion signal power.

Process 1100 involves comparing the motion signature to the reference motion signature by applying the classifier (e.g., a LDA classifier) to the motion signature. See block 1108. Although an LDA classifier is provided as an example, other classifiers described herein or known in the field may be used in some implementations instead of or in combination with an LDA. In some implementations, a feature vector is extracted from the reference motion feature, which feature vector is then provided as a data point belonging to the target class to train the LDA classifier. The LDA classifier may also be trained by additional data points belonging to the target class and additional data points belonging to the nontarget class. When more data points are provided to train the LDA classifier, the confidence of classification may be improved.

In some implementations, the motion signature is analyzed to extract a feature vector, which can then be tested using the LDA classifier to determine whether the motion signature from the instant wearer matches the reference motion feature from the reference user. The LDA classifier takes a feature vector as an input and provides a target or a non-target classification as an output.

If the feature vector extracted from the motion signature of the instant wearer is classified as the target class, it means that the motion signature matches the reference motion feature. Therefore, the process can determine that the identity of the wearer of the fitness monitor if the reference user. See block 1110.

In some implementations, when two or more motion signatures are obtained, they can be combined into one value or function, which can then be compared to the reference motion feature. In some implementations, two motion cycle profiles may be averaged, and then the average profile may be compared to a reference cycle profile. In some implementations, values of two motion signatures can form a function (e.g., power as a function of step rate), which can then be compared to a reference function. In some implementations, it is possible to classify each of the motion signatures and combine the classification results, e.g., in a probabilistic framework such as Naïve Bayes. Such a probabilistic combination is also known as Bayesian Fusion. Other probabilistic approaches instead of or in addition to Naïve Bayes (e.g., a mixture model of multiple probability functions) may also be used to combine multiple motion signatures.

Figure 12:
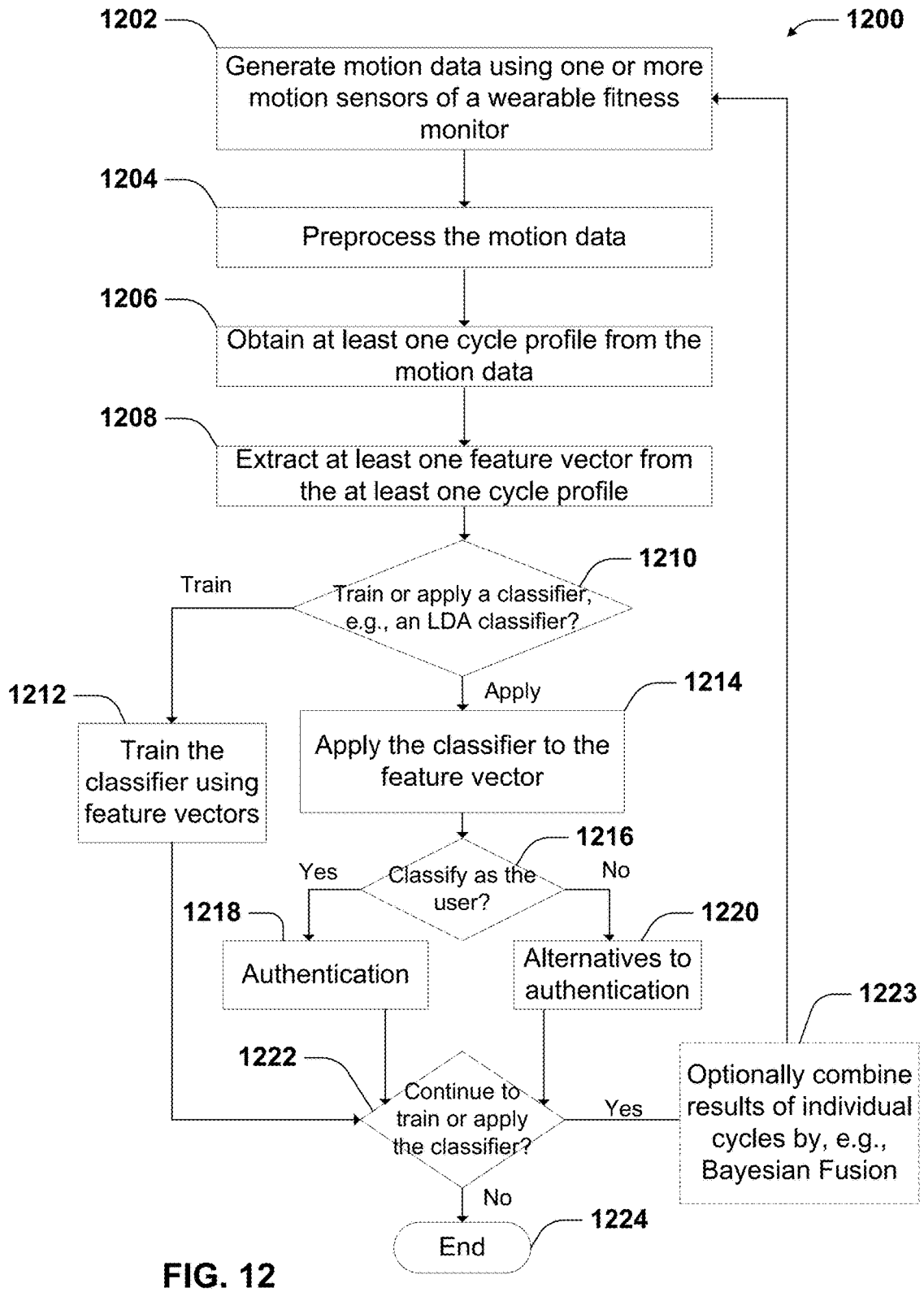
FIG. 12 shows a process 1200 for training an LDA classifier and using the classifier to authenticate a wearer based on the classification result.

FIG. 12 shows an implementation of a process 1200 for training a classifier and using the classifier to authenticate a wearer based on the classification result. Although an LDA classifier is provided as an example, other classifiers described herein or known in the field may be used in some implementations instead of or in combination with an LDA. Operation 1102 of obtaining a reference motion feature of the user may be implemented according to operations 1202, 1204, and 1206 of FIG. 12. Operation 1104 of training a linear discriminant analysis classifier may be implemented as the operations 1208 and 1112 of FIG. 12. In some implementations, operation 1106 of obtaining a motion signature may be implemented as operations 1202, 1204, and 1206. The operation 1108 of comparing the motion signature to the reference motion feature may be implemented as operation 1208 and the 1214 in FIG. 12. Operation 1110 of determining whether the motion signature matches the reference motion feature may be implemented as operation 1216 of FIG. 12.

Process 1200 starts operating one or more motion sensors of a wearable fitness monitor to generate motion data. See block 1202. In some implementations, the one or more motion sensors are selected from accelerometers, gyroscopes, magnetometers, GPS sensors, etc. In some implementations, the motion data include, for instance, about 2 minutes of data sampled at 25 Hz. In some implementations, motion data include about 5 minutes of data. In some implementations, reference data may be obtained when the wearable fitness monitor is worn by a reference user in a training phase. Then in a testing phase, data provided by an instant wearer are compared to the reference data. When the instant wearer's data match the reference data, the wearer's identity is determined to match the identity of the user, thereby providing authentication to the wearer.

For example, the owner of the wearable fitness monitor is a reference user in this context. Training data are collected from the owner of the wearable fitness monitor. In a testing phase, the wearable fitness monitor may determine whether an instant wearer of the wearable fitness monitor has the same identity as the owner, thereby authenticating the wearer as the reference user.

In some implementations, the wearable fitness monitor may experience motion caused by walking or running at various speeds. In some implementations, data from different speeds or speed ranges are used to train and generate different classifiers. Although an LDA classifier is provided as an example, other classifiers described herein or known in the field may be used in some implementations instead of or in combination with an LDA. The different classifiers will be applied for data associated with different speeds. In some implementations, data generated by motion at different speeds or speed ranges may be used to train and generate a single LDA classifier. In some implementations, data are normalized on the time dimension to obtain a single cycle profile of the motion data. In some implementations, movement speed may be provided as a feature of a feature vector, and the feature vector being provided to train the LDA classifier or test the LDA classifier.

In some imitations, motion data includes data of one, two or three motion sensors. In some imitations, each motion sensor includes three axes. In some implementations, motion data from one axis of a motion sensor are used. Such implementations can provide effective classification and efficient analysis when signal is sufficiently strong.

Figure 13:
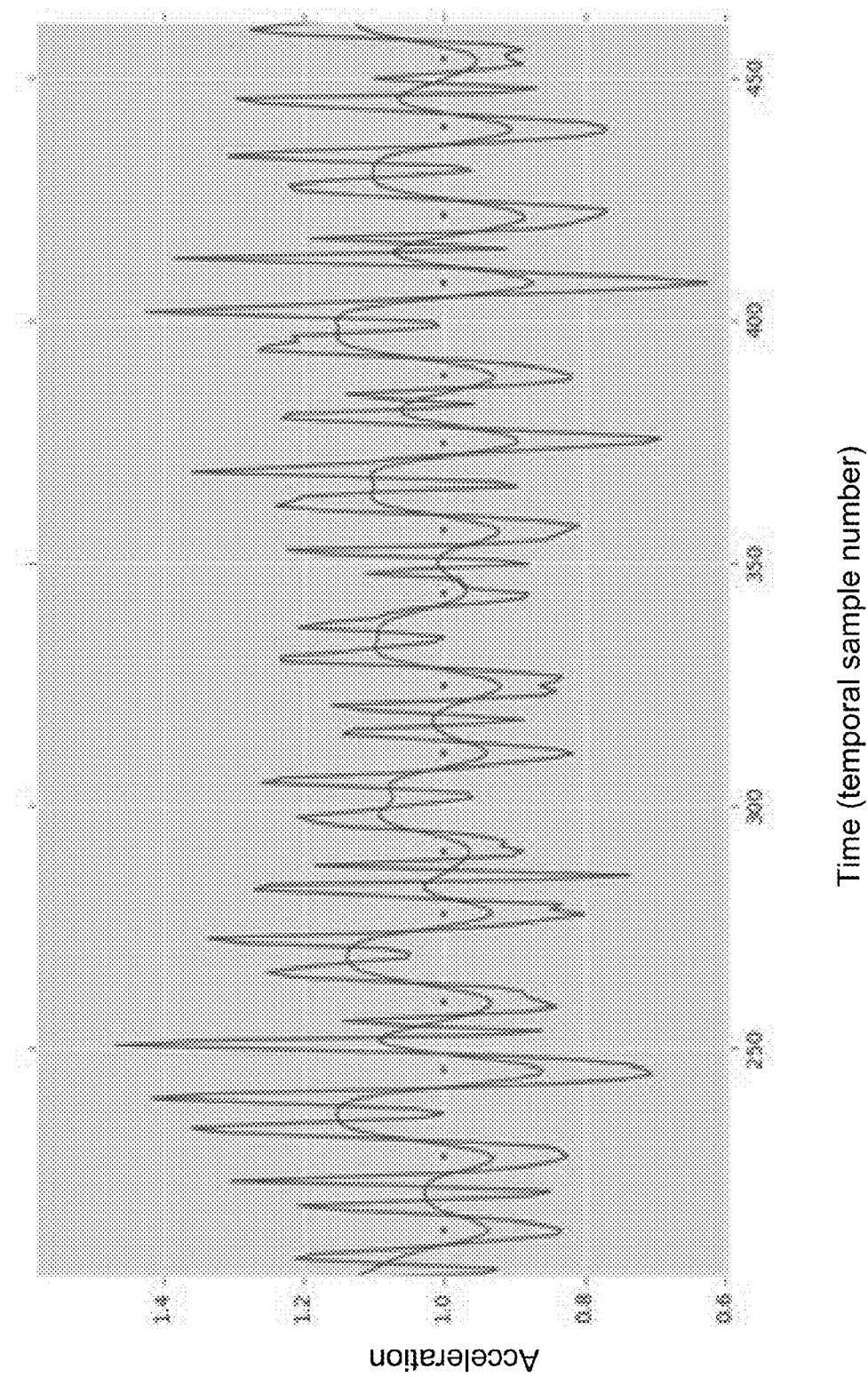
FIG. 13 shows an example of acceleration data as a function of time.
Figure 14:
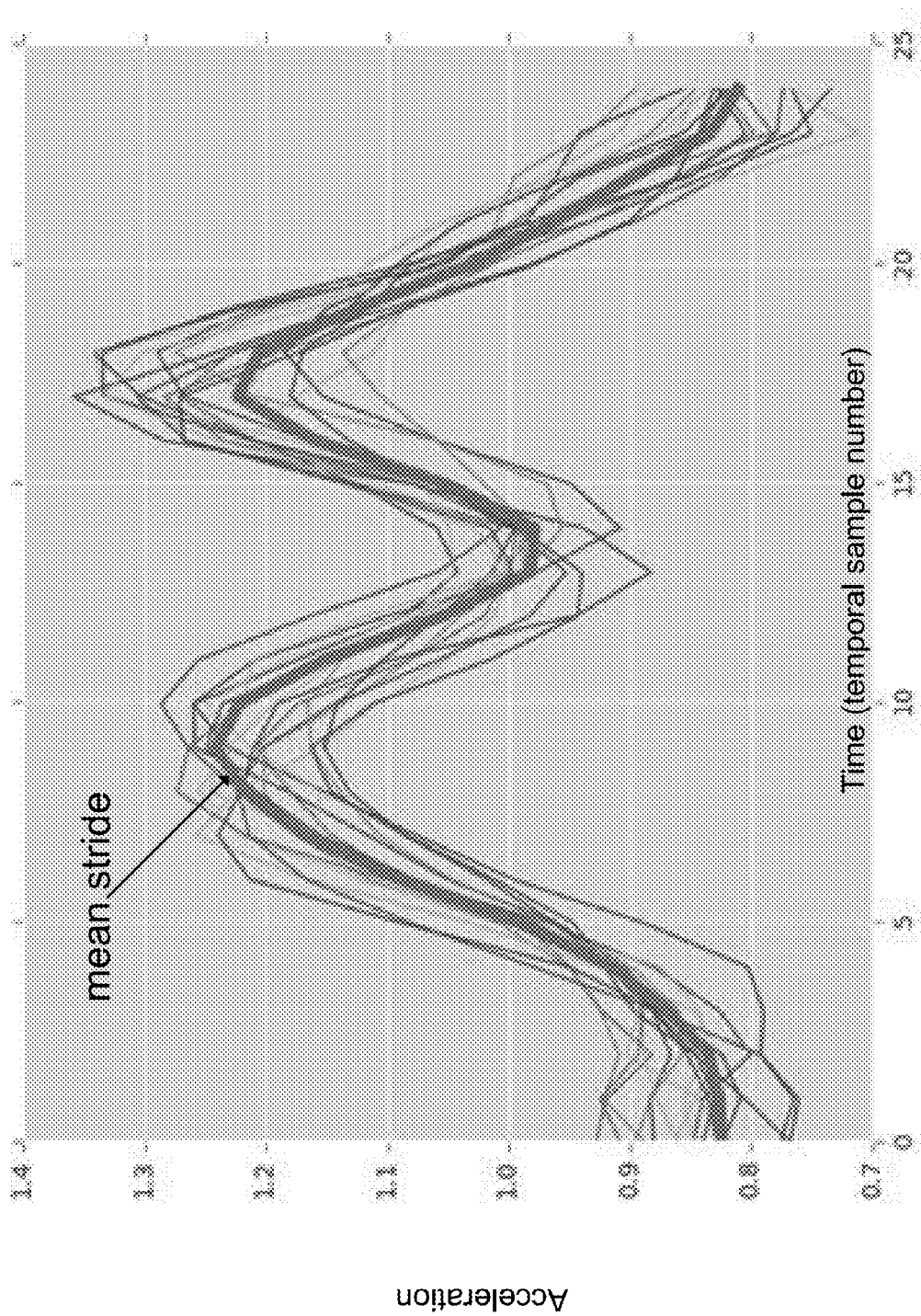
FIG. 14 shows motion data depicting multiple stride profiles from a same subject.

Process 1200 involves preprocessing motion data generated by the motion sensors using various techniques. See block 1204. In some implementations, one or more of the preprocessing techniques described herein are optional. In some implementations, raw motion sensor data are low-pass filtered to smooth the data. In some implementations, data may be smoothed by a rolling time window. In some implementations, local minima are obtained from the smoothed data. FIG. 13 shows an example of acceleration data as a function of time. As shown in the example, the filtering and smoothing provide are more regular and cyclic data. The smoothed data can then be segmented into stride profiles or cycle profiles. See block 1206 of FIG. 12. FIG. 14 shows motion data depicting multiple stride profiles from a same subject. In some implementations, data of multiple stride profiles are normalized on the time dimension. In some implementations, a profile of a mean stride is calculated from multiple strides. In some implementations, outlier profiles that deviate from the mean stride over a criterion are removed. In some implementations, a new mean stride is obtained from stride profiles having the outliers removed. In some implementations, outlier removal and averaging are performed for additional iterations to further improved representativeness of the obtained mean stride profile.

Figure 15:
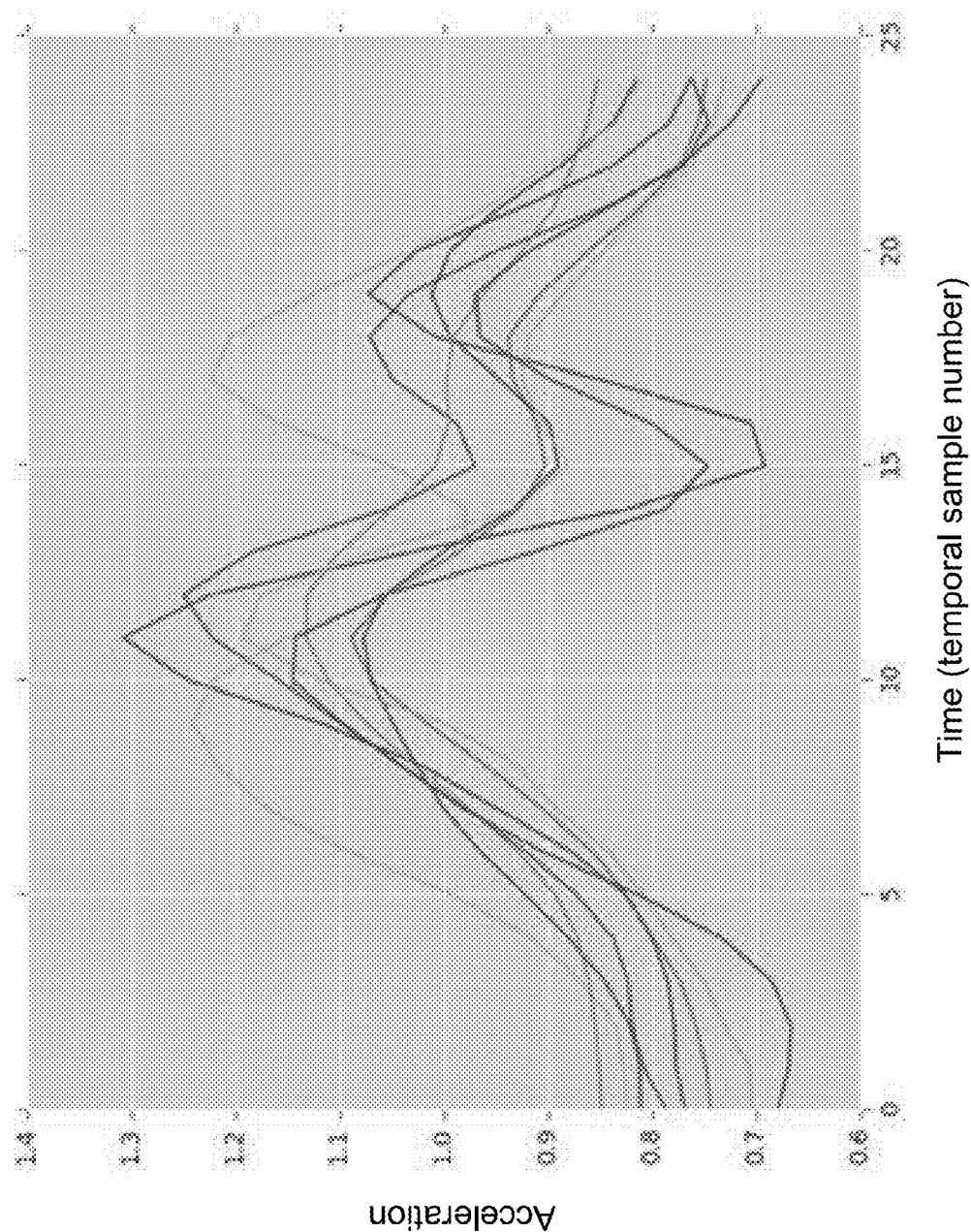
FIG. 15 shows eight mean stride cycle profiles for eight different subjects.

In some implementations, one cycle profile of a mean stride is obtained at operation 1206. In some implementations, two or more cycle profiles may be obtained from the motion data to provide training data to train the classifier. In some plantations, cycle profiles from multiple users are obtained, which are then used to train the classifier. At least one cycle profile belongs to the target class of the reference user, and at least one cycle profile belongs to the nontarget class other than the reference user. FIG. 15 shows eight mean stride cycle profiles for eight different subjects.

Process 1200 further involves extracting at least one feature vector from the at least one cycle profile. See block 1208. In some implementations, signal values based on amplitude may be used to extract features such as slopes, minima, maxima, accelerations, relative distance between features, etc. In some implementations, features may be based on moments, cumulants, time frequency domain functions, etc. In some implementations, additional features may be added to the feature vector to train or test the classifier. In some implementations, the additional features include motion data not reflected by the cycle profile. For instance, speed of motion may be used as an additional feature. In other implementations, other biometric data may be used to provide additional features of the feature vector, which can then be used to train the classifier or be tested using the classifier. For instance, heart rate, blood pressure, respiration rate, skin color, and other metrics described herein may be included as additional features.

Process 1200 further involves determining whether to train the classifier or to apply the classifier to authenticate a wearer. See block 1210. An LDA classifier is an example of a suitable classifier. Other classifiers described herein or known in the field may be used in some implementations instead of or in combination with an LDA. When the process determines to train the LDA classifier, the motion data is configured to be obtained from the reference user. The reference user's identity is the reference identity, against which an instance wearer's identity is compared to. If the instant wearer's identity matches that of the reference user, the instant wearer is authenticated as the reference user.

If the process proceeds to train the LDA classifier, feature vectors are used to train the classifier. See block 1212. The at least one cycle profile obtained in 1206, along non-target data, is used to train the LDA classifier. The at least one cycle profile is equivalent to the reference motion feature in blocks 1104, 1108, and 1110 of FIG. 11. In various implementations, at least one feature vector of a target cycle profile and at least one feature vector from a non-target cycle profile are obtained to train the LDA classifier. The target cycle profile is obtained from the reference user. The non-target profile can be obtained from a person other than the reference user. In some implementations, the non-target profile may be obtained from the reference user performing a motion that is different from a target motion. In various applications, numerous feature vectors are obtained from the reference user to train the LDA classifier. In some implementations, the multiple feature vectors obtained from the reference user provide data points of the target class. In some implementations, one or more feature vectors obtained from motion data from individuals other than the reference user are also provided as data points of the nontarget class to train the LDA classifier.

In some implementations process 1200 then determines whether to continue to train the LDA classifier with additional data. See block 1222. If the decision is positive, process 1200 returns to operation 1202 to generate more motion data using the one or more motion sensors of the wearable fitness monitor. The training LDA classifier operations described above are repeated.

In some implementations, operation 1210 decides to apply the LDA classifier to determine whether the instant wearer is the reference user. In such a case, the at least one cycle profile obtained in block 1206 is equivalent to the motion signature in blocks 1106, 1108, and 1110 in FIG. 11. The process uses the LDA classifier by applying it to the at least one feature vector. See block 1214. In effect, this operation compares the feature vector obtained from the motion data of the instant wearer to that obtained from the reference user. The LDA classifier takes the feature vector as an input and provides an output of a classification of whether or not the data belongs to the target class, i.e., the reference user. If the data is classified as belonging to the reference user, the wearable fitness monitor provides authentication to the wearer, determining that the wearer has the same identity as the reference user. See block 1218. Otherwise, the process does not provide authentication to the wearer, or requires the wearer to provide an alternative method to authenticate the wearer's identity. For instance, the wearer may be required to provide a fingerprint, password, retina scan, a heart rate measurement, or other biometric data for authenticating the wearer. In some implementations, the wearer may be required to provide more motion data to repeat the authentication operations described above.

In some implementations, process 1200 proceeds to determine whether to continue to train or use the LDA classifier. If the decision is positive, the process loops back to operation 1202 to generate more motion data to train or use the LDA classifier.

In some implementations, decision 1222 determines to continue to train the LDA classifier. Such an implementation may provide continuous learning of the classifier using data reflecting long-term change of the reference user's motion. In some implementations, the motion change may be due to physiological or environmental changes associated with the user. For instance, a user may be injured and as a result develop a different motion cycle profile. In some instances, the user may have different characteristics of motion at different times of a day. In some instances, a same user may have different cycle profile during different kinds of activities. The continue training of the LDA classifier may improve the classifier's ability to account for these different factors. In some implementations, the continual training of the LDA classifier can improve the confidence of the classification. For instance, two or more classifiers may be generated for the same user depending on certain factors, such as time of the day or activity types. In some implementations, values of additional factors may be included into the feature vector used to train the LDA classifier or other types of classifier.

In some implementations, decision 1222 operates to continue to apply the LDA classifier to multiple sets of cycle profiles. In such implementations, each set of cycle profiles may be classified by the classifier. Then multiple classification results can be combined by probabilistic methods to obtain a final classification result. The multiple classification results may be combined by Bayesian Fusion using Naïve Bayes. See block 1223 outlined by dashed lines indicating an optional operation. The final classification result can then be used to determine if a user should be authenticated. In such an implementation, the authentication of 1218 is modified to be contingent on the final classification result meeting an authentication criterion.

Finally, process 1200 can determine not to continue to train or use the LDA classifier, and the process comes to an end at block 1224.

Figure 16:
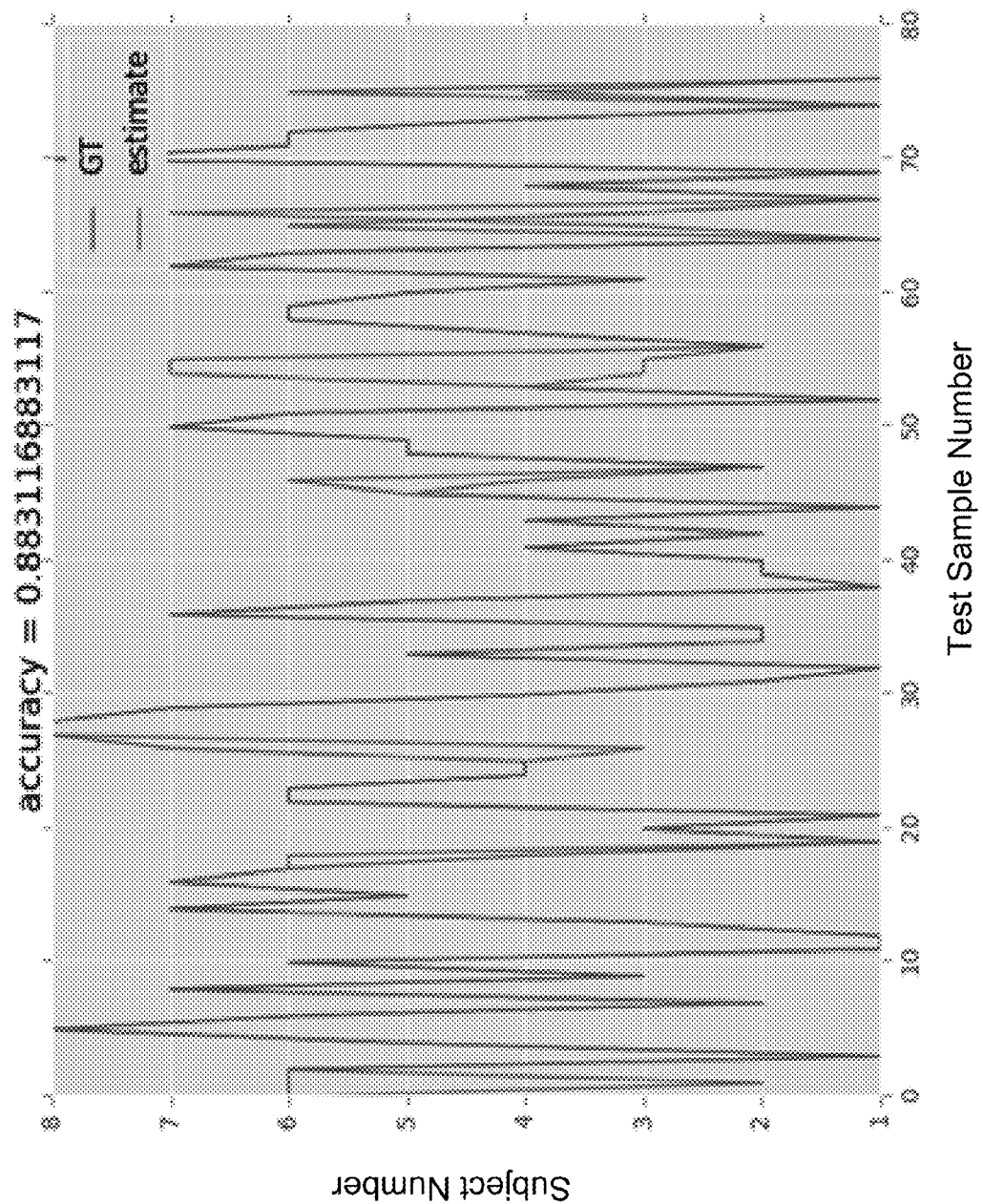
FIG. 16 shows an example of classification results for two-minute walking data for eight subjects.

FIG. 16 shows example classification results for two-minute walking data (fs=25 Hz) for 8 subjects. The data set is randomly divided into training and testing sets. The graph shows the performance of the classifier on these 8 subjects.

Systems

In one embodiment, the wearable fitness monitor is one component of a system that comprises a secondary device capable of communicating with the wearable fitness monitor. In some implementations, the secondary device may be a smart phone, a PDA, a tablet, or a computer. In some implementations, the secondary device may have a shape and mechanical and/or magnetic interface to accept the wearable fitness monitor for safe keeping, communication, and/or charging. Notably, the communication between the wearable fitness monitor and the secondary device may be provided through wireless communication techniques/methods and protocols mentioned elsewhere herein. In some implementations, a secondary device performs the biometric matching between a wearer's motion signature and a user's reference feature.

In some implementations, the secondary device may comprise sensors to assist in biometric or environmental monitoring such as, for example, sensors that measure ambient light, noise and/or sound (e.g., to detect snoring), temperature, humidity, and air quality (pollen, dust, $CO_2$, etc.). In one embodiment, the secondary device may communicate with an external service such as www.fitbit.com or server (e.g., personal computer). Communication may be achieved through wired or wireless circuitry and protocols to transfer data to and/or from the secondary device. As examples, any of the wireless technologies described above for the fitness monitor may be used. The secondary device may also act as a relay to transfer data to and/or from the wearable fitness monitor to an external service such as www.fitbit.com or other service (e.g., news, social network updates, email, calendar notifications). Calculation of the user's fitness data may be executed on one or both devices or an external service (e.g., a cloud server) using data from one or both devices.

In some implementations, one or more of the operations performed to identify a user are performed on a secondary device. It should be understood that some or all of the operations may be performed on the wearable fitness monitor. Often, the operations are divided between the wearable fitness monitor and the secondary device.

As mentioned above, the wearable fitness monitor may be used as a proxy to authorize a credit card or other secure service. Moreover, data of the wearable fitness monitor for an authorized user may be compared to the user's data of a smart phone. The comparison results may be used to authorize a user. Based on the data from the wearable fitness monitor and/or the smart phone, a user may be authorized, deauthorized, and or reauthorized. In some implementations, the authorization, deauthorization, and reauthorization may be performed "online" on the wearable fitness monitor. In such cases, the classifier logic may execute on the wearable fitness monitor. In other implementations, the authorization, deauthorization, and reauthorization may be performed on the smart phone. In such cases, the classifier logic may execute on the smart phone. In further implementations, the authorization, deauthorization, and reauthorization may be performed "offline" on a back end server over a network. In such cases, the classification logic may be implemented on the back-end servers. In yet other implementations, the authorization, deauthorization, and reauthorization may be performed using the wearable fitness monitor, the smart phone, and the back end server. In such cases, portions of the classification logic is split among those devices/systems.

The techniques and functions outlined above may be implemented in a wearable fitness monitor as machine-readable instruction sets, either as software stored in memory, as application-specific integrated circuits, field-programmable gate-arrays, or other mechanisms for providing system control. Such instruction sets may be provided to a processor or processors of a wearable fitness monitor to cause the processor or processors to control other aspects of the wearable fitness monitor to provide the functionality described above.

Unless the context (where the term "context" is used per its typical, general definition) of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein.

There are many concepts and implementations described and illustrated herein. While certain features, attributes and advantages of the implementations discussed herein have been described and illustrated, it should be understood that many others, as well as different and/or similar implementations, features, attributes and advantages of the present inventions, are apparent from the description and illustrations. As such, the above implementations are merely exemplary. They are not intended to be exhaustive or to limit the disclosure to the precise forms, techniques, materials and/or configurations disclosed. Many modifications and variations are possible in light of this disclosure. It is to be understood that other implementations may be utilized and operational changes may be made without departing from the scope of the present disclosure. As such, the scope of the disclosure is not limited solely to the description above because the description of the above implementations has been presented for the purposes of illustration and description.

Notably, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

None of the pending claims include limitations presented in "means plus function" or "step plus function" form. (See, 35 USC § 112(f)). It is Applicant's intent that none of the claim limitations be interpreted under or in accordance with 35 U.S.C. § 112(f).

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method, implemented on a wearable fitness monitor comprising one or more motion sensors and one or more processors, the method comprising:
    (a) obtaining motion data of a wearer from the one or more motion sensors when the wearable fitness monitor is worn by the wearer, wherein the wearable fitness monitor is configured to be worn by a person;
    (b) obtaining, by the one or more processors, a motion signature using the motion data of the wearer, wherein the motion signature characterizes a body movement;
    (c) obtaining, by the one or more processors, a test feature vector from the motion signature;
    (d) applying, by the one or more processors, a machine learning classifier to the test feature vector, wherein
        the machine learning classifier was trained using motion data reflecting motions of one or more non-humans or one or more humans,
        the machine learning classifier is configured to receive feature vectors as inputs and provide classifications of the feature vectors as outputs, and
        the classifications indicate whether the feature vectors are obtained from non-humans;
    (e) obtaining, using the machine learning classifier and by the one or more processors, a classification indicating whether the test feature vector is obtained from a non-human;
    (f) determining, based on the classification obtained in (e) and by the one or more processors, the motion signature corresponds to an invalid motion feature, the invalid motion feature characterizing motion likely to be performed by a non-human; and
    (g) preventing, based on the determination in (f) and by the one or more processors, the wearable fitness monitor from allowing a transaction.

2. The method of claim 1, wherein the transaction comprises accessing a secure item or providing an award for meeting an activity threshold to a user associated with the wearable fitness monitor.

3. The method of claim 1, further comprising, responsive to determining that the motion signature corresponds to the invalid motion feature, requiring the wearer to authenticate himself or herself.

4. The method of claim 3, wherein requiring the wearer to authenticate comprises requiring the wearer to input a passcode, a fingerprint, an iris image, an ECG, a facial image, a vocal message, or any combination thereof.

5. The method of claim 1, wherein determining the motion signature corresponds to an invalid motion feature in (e) comprises: obtaining an additional signature using data from one or more additional sensors, and determining that the motion signature, the additional signature, or a combination thereof is inconsistent with at least one human activity.

6. The method of claim 1, wherein the invalid motion feature is a periodic motion having a cycle-to-cycle consistency greater than a threshold.

7. The method of claim 1, wherein the motion signature characterizes a cycle of periodic movement of a person wearing the wearable fitness monitor.

8. The method of claim 7, wherein the periodic movement is selected from the group consisting of running, walking, cycling, swimming, weight lifting, climbing, rowing, a gymnastic exercise, dancing, an aerobic exercise, a yoga routine, golfing, swinging a club, swinging a racquet, striking a ball or another object, swimming, diving, surfing, skating, skiing, skate boarding, exercising on a machine, driving a vehicle, and riding an animal.

9. The method of claim 1, wherein the obtaining the motion signature using the motion data of the wearer further comprises: obtaining a cycle profile from the motion data.

10. The method of claim 9, wherein the obtaining the test feature vector from the motion signature of (c) comprises: extracting one or more features from the cycle profile or values derived from the cycle profile, and combining one or more features into the feature vector.

11. The method of claim 10, wherein each feature is selected from the group consisting of: a slope, an inflection, a zero crossing, a derivative, a moment, a cumulant, and any combination thereof.

12. The method of claim 1, wherein the machine learning classifier comprises a linear discriminant analysis classifier.

13. The method of claim 1, wherein the machine learning classifier comprises a neural network classifier.

14. A system comprising:
a wearable fitness monitor configured to be worn by a person and comprising:
one or more motion sensors, and
a communication interface configured for communicating data from the one or more motion sensors to a device external to the wearable fitness monitor; and
logic configured to:
(a) obtain motion data of a wearer from the one or more motion sensors when the wearable fitness monitor is worn by the wearer, wherein the wearable fitness monitor is configured to be worn by a person;
(b) obtain a motion signature using the motion data of the wearer, wherein the motion signature characterizes a body movement;
(c) obtain a test feature vector from the motion signature;
(d) apply a machine learning classifier to the test feature vector, wherein
the machine learning classifier was trained using motion data reflecting motions of one or more non-humans or one or more humans,
the machine learning classifier is configured to receive feature vectors as inputs and provide classifications of the feature vectors as outputs, and
the classifications indicate whether the feature vectors are obtained from non-humans;
(e) obtain, using the machine learning classifier, a classification indicating whether the test feature vector is obtained from a non-human;
(f) determine, based on the classification obtained in (e), the motion signature corresponds to an invalid motion feature, the invalid motion feature characterizing motion likely to be performed by a non-human; and
(g) prevent, based on the determination in (f), the wearable fitness monitor from allowing a transaction.

15. The system of claim 14, wherein the transaction comprises accessing a secure item or providing an award for meeting an activity threshold to a user associated with the wearable fitness monitor.

16. The system of claim 15, wherein the logic is further configured to: responsive to determining that the motion signature corresponds to the invalid motion feature, require the wearer to authenticate himself or herself.

17. The system of claim 16, wherein requiring the wearer to authenticate comprises requiring the wearer to input a passcode, a fingerprint, an iris image, an ECG, a facial image, a vocal message, or any combination thereof.

18. The system of claim 14, wherein determining the motion signature corresponds to an invalid motion feature in (e) comprises: obtaining an additional signature using data from one or more additional sensors, and determining that the motion signature, the additional signature, or a combination thereof is inconsistent with at least one human activity.

19. The system of claim 14, wherein the machine learning classifier comprises a linear discriminant analysis classifier.

20. The system of claim 14, wherein the machine learning classifier comprises a neural network classifier.

* * * * *